US012605468B2

(12) United States Patent
Gibbs et al.

(10) Patent No.: US 12,605,468 B2
(45) Date of Patent: Apr. 21, 2026

(54) OXAZINE-BASED FLUOROPHORE COMPOUNDS FOR NERVE-SPECIFIC IMAGING

(71) Applicant: Oregon Health & Science University, Portland, OR (US)

(72) Inventors: Summer L. Gibbs, West Linn, OR (US); Lei G. Wang, Portland, OR (US); Connor W. Barth, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 853 days.

(21) Appl. No.: 17/794,932

(22) PCT Filed: Jan. 22, 2021

(86) PCT No.: PCT/US2021/014740

§ 371 (c)(1),
(2) Date: Jul. 22, 2022

(87) PCT Pub. No.: WO2021/150979

PCT Pub. Date: Jul. 29, 2021

(65) Prior Publication Data

US 2023/0148317 A1 May 11, 2023

Related U.S. Application Data

(60) Provisional application No. 62/965,519, filed on Jan. 24, 2020.

(51) Int. Cl.

| | |
|---|---|
| ***C07D 265/14*** | (2006.01) |
| ***A61K 49/00*** | (2006.01) |
| ***C07D 265/38*** | (2006.01) |
| ***C07D 413/04*** | (2006.01) |
| ***C07D 413/14*** | (2006.01) |
| ***C07D 498/04*** | (2006.01) |
| ***C07D 498/14*** | (2006.01) |

(52) U.S. Cl.

CPC ........ *A61K 49/0028* (2013.01); *C07D 265/38* (2013.01); *C07D 413/04* (2013.01); *C07D 413/14* (2013.01); *C07D 498/04* (2013.01); *C07D 498/14* (2013.01)

(58) Field of Classification Search

None

See application file for complete search history.

(56) References Cited

U.S. PATENT DOCUMENTS

| | | | |
|---|---|---|---|
| 3,824,074 | A | 7/1974 | Bugaut et al. |
| 3,896,117 | A | 7/1975 | Bugaut et al. |
| 4,288,227 | A | 9/1981 | Gertisser et al. |
| 4,847,177 | A | 7/1989 | Raue et al. |
| 5,733,343 | A | 3/1998 | Mockli |
| 8,206,464 | B2 | 6/2012 | Cremer et al. |
| 8,679,776 | B2 | 3/2014 | Miller |
| 9,796,730 | B2 | 10/2017 | Kesenheimer et al. |
| 10,495,632 | B2 | 12/2019 | Lavis et al. |
| 2007/0031336 | A1 | 2/2007 | Auberson et al. |
| 2009/0036437 | A1 | 2/2009 | Hara et al. |
| 2010/0297684 | A1 | 11/2010 | Miller |
| 2011/0094566 | A1 | 4/2011 | Calzaferri |
| 2014/0079635 | A1 | 3/2014 | Wang |
| 2016/0263249 | A1 | 9/2016 | Frangioni et al. |
| 2017/0045501 | A1 | 2/2017 | Lavis et al. |
| 2017/0088534 | A1 | 3/2017 | Clunas et al. |
| 2017/0176469 | A1 | 6/2017 | Wang |

FOREIGN PATENT DOCUMENTS

| | | | | |
|---|---|---|---|---|
| CN | 106471067 A | 3/2017 | |
| CN | 110099671 A | 8/2019 | |
| JP | S3045477 A | 4/1978 | |
| JP | 2007502798 A | 2/2007 | |
| JP | WO2006087935 A1 | 7/2008 | |
| JP | 2017503004 A | 1/2017 | |
| JP | 2017519844 A | 7/2017 | |
| WO | WO-2005016934 A1 * | 2/2005 | ........... C07D 513/14 |
| WO | 2009120416 A1 | 10/2009 | |
| WO | WO2010054183 A2 | 5/2010 | |
| WO | 2015066296 A1 | 5/2015 | |
| WO | WO2018115154 A1 | 6/2018 | |
| WO | WO2020023911 A2 | 1/2020 | |

OTHER PUBLICATIONS

Canadian Office Action mailed Dec. 21, 2023 for Canadian Application No. 3,164,184, a foreign counterpart to U.S. Appl. No. 17/794,932, 7 pages.

"PubChem CID 123155710" Create Date: Jan. 24, 2017, Date Accessed: Jul. 22, 2022; p. 2.

CAS Registry No. 846022-19-3, C20H22N302-CI, 2H-1,4-Oxazino[2,3-b]pyrido[2,3-i]phenoxazin-6-ium,8-ethyl-3,4,8,9,10,11-hexahydro-4-methyl-,chloride(9CI) compound of Example No. 2 (p. 5, [0093]) in US 2007/0031336 A1, Published Feb. 8, 2007, Auberson et al.

CAS Registry No. 846022-20-6, C18H18N303, 2H,8H-Bis[1,4]oxazino[2,3-b:3',2'-i]phenoxazin-6-ium,3,4,9,10-tetrahydro-4,8-dimethyl (9Cl), a NaBF4—salt of page 12 in US 2014/0079635 A1, published Mar. 20, 2014, Wang et al.

Choi et al., "Silicon substitution in oxazine dyes yields near-infrared azasiline fluorophores that absorb and emit beyond 700 nm," 2018. Organic Letters, 20:4482-4485.

Ge et al., "Discovery of novel benzo[a]phenoxazine SSJ-183 as a drug candidate for malaria," Jul. 2010. ACS Med. Chem. Lett., 1:360-364.

Ge et al., "Synthesis and in vitro antiprotozoal activies of water-soluble, inexpensive 3,7-Bis(dialkylamino) phenoxazin-5-ium derivatives," May 2008. J. Med. Chem., 51:3654-3658.

Ge et al., "The convenient syntesis of zinc chloride-free 3,7-bis(dialkylamino)phenoxazinium salts," Jan. 2008. Dyes and Pigments, 79:33-39.

(Continued)

*Primary Examiner* — Nissa M Westerberg

(74) *Attorney, Agent, or Firm* — Lee & Hayes, P.C.

(57) ABSTRACT

This invention concerns novel oxazine-based fluorophore compounds useful in in vivo nerve imaging, as well as compositions comprising them and methods for their use.

11 Claims, 11 Drawing Sheets

(56) References Cited

OTHER PUBLICATIONS

Ge et al., "Third-order nonlinear optical properties of symmetric phenoxazinium chlorides with resonance structures at 532 nm," Apr. 2011. Dyes and Pigments, 91:489-494.
Ge et al., "Third-order nonlinear optical properties of a new type of D-pi-D unsymmetrical phenoxazinium chloride with ersonance structures," Feb. 2011. Chemical Physics, 382:74-79.
Gibbs-Strauss et al., "Nerve-highlighting fluorescent contrast agents for image-guided surgery," Apr. 2011. Mol. Imaging, 10(2):91-101.
Grimm et al., "A general method to improve fluorophores for live-cell and single-molecule microscopy," Mar. 2015. Nature Methods, 12(3):244-253.
Hintersteiner et al., "In vivo detection of amyloid-beta deposits by near-infrared imaging using an oxazine-derivative probe," May 2005. Nature Biotechnology, 23(5):577-583.
Li et al., "Third-order nonlinear optical properties of a pi-conjugated phenoxazinium compund: Mechanism and dynamic response," Feb. 2013. Materials Chenimatry and Physics, 139:975-978.
Mennigmann et al., "Dependence of the mutagenic power of heteroatomic dyes on their DNA-base-pair specificity," 1981. Mutation Research, 91:183-191.
Muller et al., "Interactions fo heteroaromatic compounds with nucleic acids: The influence of heteroatoms and polarizability on the base specificity of intercalating ligands," 1975. Eur. J. Biochem, 54:267-277.
Shui et al., "Solvent effect induced solute damage in an organic inner salt," Dec. 2010. Optics Express, 18(26):17 pages.
Takasu et al., "Synthesis and antimalarial property of orally active phenoxazinium salts," May 2007. Journal of Medicinal Chemistry, 50(10):2281-2284.
Yang et al., "Pharmacodynamics and pharmacokinetics studies of phenoxazinium derivatives for antimalarial agent," Jan. 2009. Bioorganic & Medicinal Chemistry, 17:1481-1485.
Yang et al., "Selective ratiometric detection of Hg2+ in pure water using a phenoxazinium-based probe," Mar. 2011. Tetrahedron Letters, 52:2492-2495.
Office Action for Canadian Application No. 3,164,184, Dated Aug. 20, 2024, 5 pages.
Search Report and Written Opinion for European Application No. 21744773.9, Dated Jul. 24, 2024, 11 pages.
Wang, et al., "Investigation of Oxazine and Rhodamine Derivatives as Peripheral Nerve Tissue Targeting Contrast Agent for In Vivo Fluorescence", Progress in Biomedical Optics and Imaging, SPIE—International Society for Optical Engineering, vol. 10862, Mar. 7, 2019, pp. 108620H-108620H.
Office Action for Chinese Application No. 202180010674.8, Dated Feb. 19, 2025, 23 pages.
Office Action for Japanese Application No. 2022-544656, Dated Dec. 26, 2024, 10 pages.
Office Action for Japanese Application No. 2022-544656, Dated May 29, 2025, 4 pages.
Office Action for Chinese Application No. 202180010674.8, Dated Sep. 5, 2025, 8 pages.
Office Action for Korean Application No. 10-2022-7028755, Dated Aug. 26, 2025, 7 pages.

* cited by examiner

OXAZINE-BASED FLUOROPHORE COMPOUNDS FOR NERVE-SPECIFIC IMAGING

CROSS-REFERENCE TO RELATED APPLICATION

This is the 371 National Phase of International Application No. PCT/US2021/014740, filed Jan. 22, 2021, which claims priority to and the benefit of the earlier filing of U.S. Provisional Application No. 62/965,519, filed on Jan. 24, 2020, which is incorporated by reference herein in its entirety.

STATEMENT REGARDING FEDERALLY SPONSORED RESEARCH OR DEVELOPMENT

This invention was made with government support under grant R01 EB021362 awarded by the National Institutes of Health. The government has certain rights in the invention.

FIELD OF THE DISCLOSURE

This invention concerns novel oxazine-based fluorophore compounds useful in in vivo nerve imaging, as well as compositions comprising them and methods for their use.

BACKGROUND OF THE INVENTION

Over 300 million surgeries are performed worldwide each year. Despite many recent advances in the treatment of cancer and other diseases, surgery remains the most effective treatment option for a number of diseases and injuries. The ultimate goal of surgery is to remove or repair tissues while minimizing comorbidities by preserving vital structures such as nerves and blood vessels. Recent technological advances including minimally invasive robot assisted laparoscopic surgery have improved outcomes and made it possible to perform difficult procedures robustly with minimal risk. Furthermore, preoperative three-dimensional imaging technologies such as magnetic resonance imaging (MRI) and computed tomography (CT) have vastly improved diagnostic accuracy, staging, and preoperative planning.

While advances have been made, identifying vital structures for preservation (e.g., nerves) or tissue for complete resection (e.g., tumors) during surgical procedures remains difficult. Nerve identification and sparing can be difficult intraoperatively due to variations in patient anatomy and often little ability for direct nerve visualization in the surgical field. Currently, intraoperative nerve detection is performed through a combination of naked eye visualization, palpation, and electromyographic monitoring. Several imaging modalities have been utilized in clinical studies for nerve detection including ultrasound, optical coherence tomography, and confocal endomicroscopy. However, these lack specificity, resolution, and wide-field imaging functionality, making it difficult to identify nerve tissues in real time. As a result, nerve damage continues to plague surgical outcomes. latrogenic nerve injury affects up to 63 million patients worldwide annually, causing acute and chronic pain as well as impairment or loss of motor and sensory function. Radical prostatectomy (RP), a surgical procedure involving removal of the entire prostate as a prostate cancer cure, is particularly plagued by nerve damage. Furthermore, while minimally invasive methods, such as robotic assisted RP, can achieve equivalent cancer control to open RP while resulting in decreased blood loss, lower transfusion rate, and faster convalescence, these advances provide no benefit in nerve-sparing outcomes and in fact, remove the ability to directly palpate the tissue.

An imaging modality capable of wide field, real time identification of nerve tissues intraoperatively would greatly benefit surgeons in nerve preservation and reduce rates of iatrogenic nerve injury, improving quality of life for patients post-surgery.

Currently, no NIR nerve-specific fluorophore exists and further fluorophore development is required to obtain a proper candidate for clinical translation. Several classes of nerve specific fluorophores have been studied for FGS. See, for instance: Gibbs-Strauss et al. Molecular imaging 10, 91-101 (2011); Wu et al. Journal of medicinal chemistry 51, 6682-6688 (2008); Wang et al. The journal of histochemistry and cytochemistry: official journal of the Histochemistry Society 58, 611-621 (2010); Gibbs et al. PloS one 8, e73493 (2013); Stankoff et al. Proceedings of the National Academy of Sciences of the United States of America 103, 9304-9309 (2006); Cotero et al. Molecular imaging and biology: MIB: the official publication of the Academy of Molecular Imaging 14, 708-717 (2012); Cotero et al. PloS one 10, e0130276 (2015); Bajaj et al. The journal of histochemistry and cytochemistry: official journal of the Histochemistry Society 61, 19-30 (2013); Gibbs-Strauss et al. Molecular imaging 9, 128-140 (2010); Meyers et al. The Journal of neuroscience: the official journal of the Society for Neuroscience 23, 4054-4065 (2003); Wang et al. The Journal of Neuroscience: the official journal of the Society for Neuroscience 31, 2382-2390 (2011); and Park et al. Theranostics 4, 823-833 (2014). Of these, Oxazine 4 is the most promising candidate for development, showing high nerve-specificity and red shifted absorption and emission spectra close to the NIR (Park et al. Theranostics 4, 823-833 (2014)).

Useful oxazine nerve-sparing fluorophores are disclosed in International Application PCT/US2019/045347, but there remains a need for such compounds, particularly for use in aqueous compositions.

BRIEF SUMMARY OF THE INVENTION

One embodiment provides a compound of Formula (1):

(I)

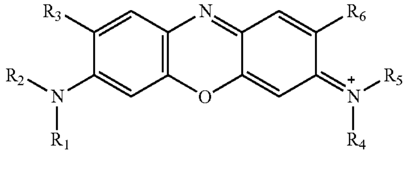

wherein:

$R_1$ and $R_2$ are each independently selected from the group of straight or branched $C_1$-$C_6$ alkyl; $-(CH_2)_{n1}-SO_3^-$, $-(CH_2)_{n1}-N{+}(CH_3)_3$, $-CH_2-CH_2-O-X_1$, $-CH_2-CH_2-O-[CH_2-CH_2-O]_{n2}-X_1$, $-CH_2-CH_2-CH_2-O-X_1$, and $-CH_2-CH_2-CH_2-O-[CH_2-CH_2-CH_2-O]_{n3}-X_1$; or a moiety selected from the group of:

a)

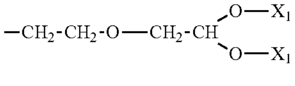

;

-continued b)

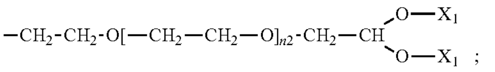

c)

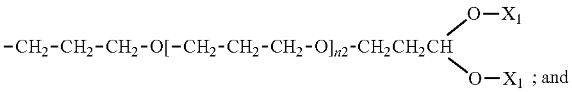

d)

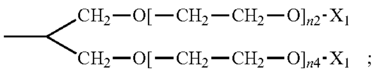

$R_3$ is hydrogen or $R_2$ and $R_3$ together form a fused ring, creating a core of Formula (II):

(II)

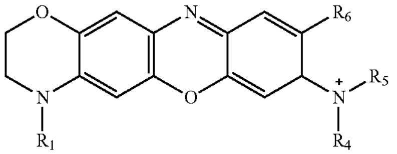

$R_4$ and $R_5$, together with the nitrogen atom to which they are bound, form a ring selected from the group of:

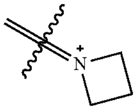

and

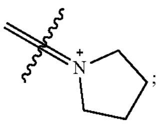

or, when the compound is of Formula (II), $R_4$ and $R_5$ may be independently selected from $C_1$-$C_6$ alkyl, with the proviso that, when $R_1$ is methyl and $R_4$ is ethyl, $R_5$ is not ethyl;

$R_6$ is hydrogen;

or, when $R_2$ and $R_3$ together form a fused ring to create a core of Formula (II), $R_5$ and $R_6$ may also, together with the nitrogen atom to which $R_5$ is bound, form a fused ring, creating a core of Formula (III):

(III)

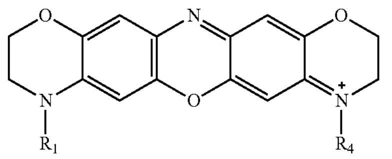

with the proviso that, when $R_4$ and $R_5$, together with the nitrogen atom to which they are bound, form the ring

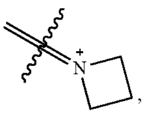 [SMILES: *=[N+]1CCC1]

and $R_3$ is H, $R_1$ and $R_2$, together with the nitrogen atom to which they are bound, may form a pyrrolidinyl ring;

$X_1$ in each instance is independently selected from $C_1$-$C_6$ straight or branched alkyl, $C_1$-$C_6$ straight or branched alkenyl, $C_1$-$C_6$ straight or branched alkynyl, and —Si($C_1$-$C_4$ alkyl)$_3$;

n is an integer selected from the group of 1 and 2;

n1 is an integer independently selected in each instance from the group of 1, 2, 3, and 4;

n2 is an integer independently selected in each instance from the group of 1, 2, 3, 4, 5, 6, 7, 8, 9, and 10;

n3 is an integer independently selected in each instance from the group of 1, 2, 3, 4, 5, 6, 7, 8, 9, and 10;

n4 is an integer independently selected in each instance from the group of 1, 2, 3, 4, 5, 6, 7, 8, 9, and 10; and with the proviso that the sum of n2+n2 is not greater than 10;

with the proviso that the sum of n2+n3 is not greater than 10;

with the proviso that the sum of n2+n4 is not greater than 10;

with the proviso that the sum of n3+n4 is not greater than 10;

with the proviso that, when $R_4$ and $R_5$, together with the nitrogen atom to which they are bound, form the ring

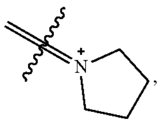 [SMILES: *=[N+]1CCCC1]

$R_1$ and $R_2$ are not both methyl, $R_1$ and $R_2$ are not both ethyl, $R_1$ and $R_2$ are not both n-propyl, $R_1$ and $R_2$ are not both n-butyl, and $R_1$ and $R_2$ are not both n-pentyl; and with the proviso that, when the compound is of Formula (III), when $R_1$ is methyl, $R_4$ is not methyl.

DETAILED DESCRIPTION OF THE INVENTION

Figure 1A:
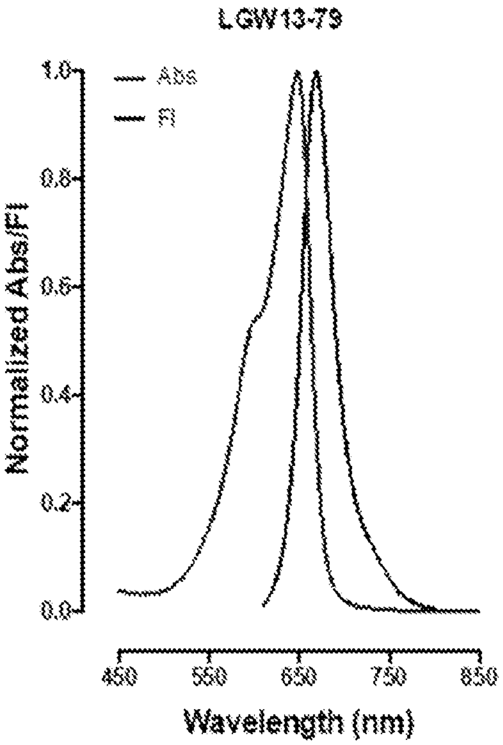
FIGS. 1A-1F represents normalized absorption and fluorescence emission spectra of oxazine derivatives in PBS, respectively those for compounds (FIG. 1A) LGW13-79, (FIG. 1B) LGW14-42, (FIG. 1C) LGW14-47, (FIG. 1D) LGW14-51, (FIG. 1E) LGW14-53, and (FIG. 1F) LGW14-83.
Figure 1B:
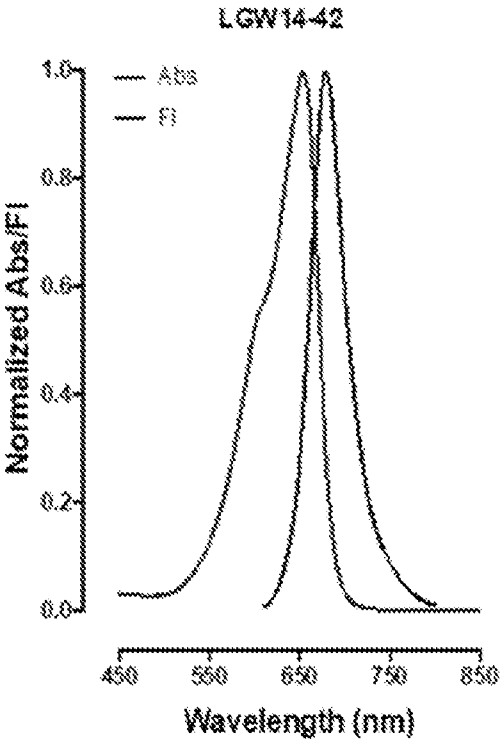
Figure 1C:
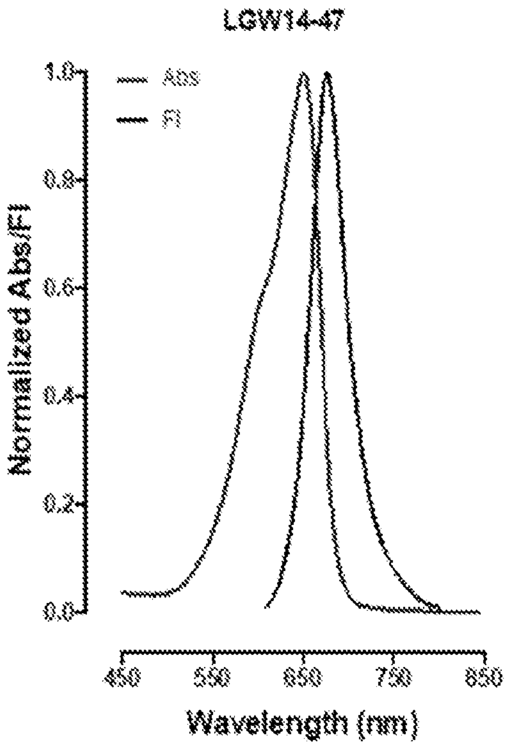
Figure 1D:
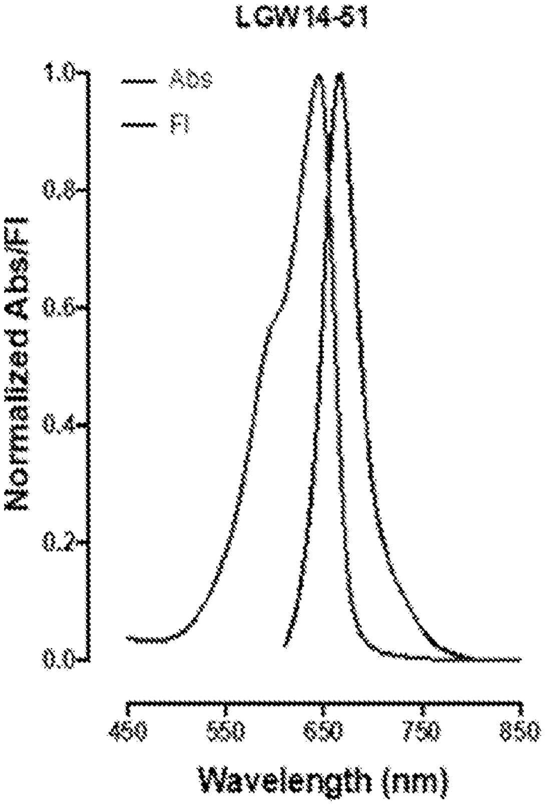
Figure 1E:
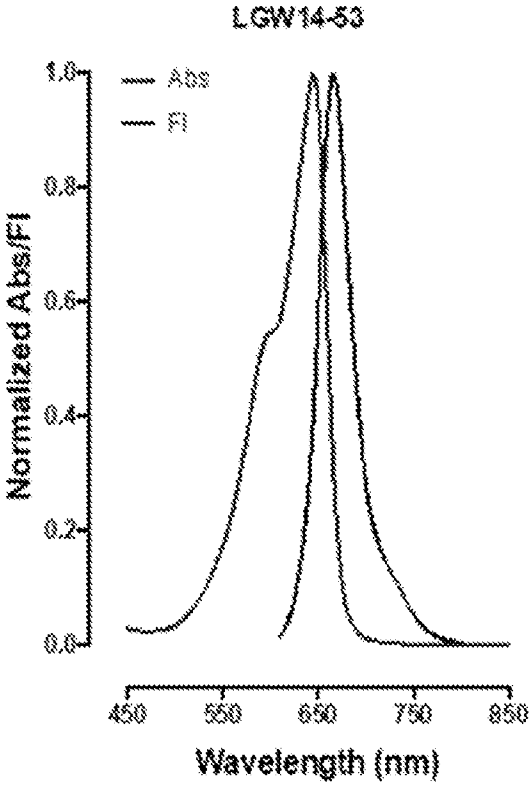
Figure 1F:
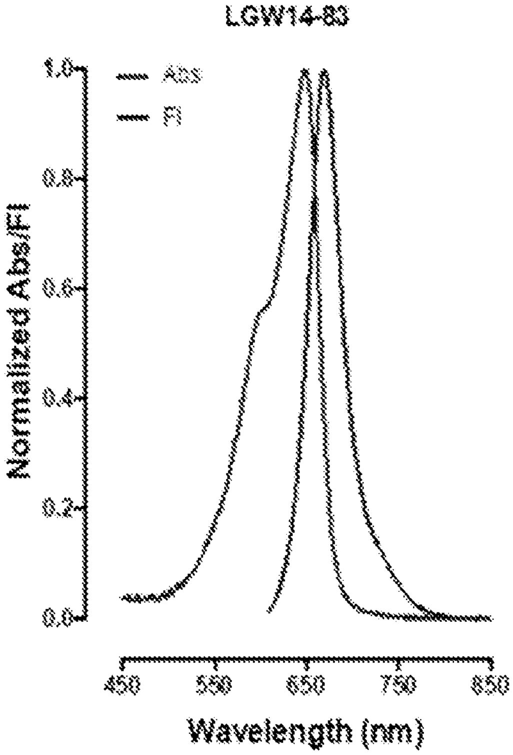

A second embodiment provides a compound of Formula (IV):

(IV)

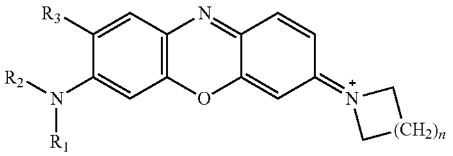

wherein:

$R_1$ and $R_2$ are each independently selected from the group of straight or branched $C_1$-$C_6$ alkyl;

$-(CH_2)_{n1}-SO_3$, $-(CH_2)_{n1}-N+(CH_3)_3$, $-CH_2-CH_2-O-X_1$, $-CH_2-CH_2-O-[CH_2-CH_2-O]_{n2}-X_1$, $-CH_2-CH_2-CH_2-O-X_1$, and $-CH_2-CH_2-CH_2-O-[CH_2-CH_2-CH_2-O]_{n3}-X_1$; or a moiety selected from the group of:

a)

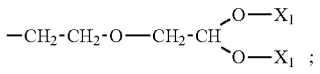

b)

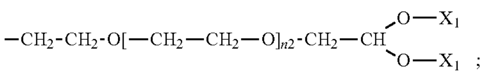

c)

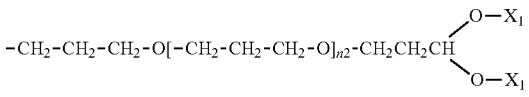

; and d)

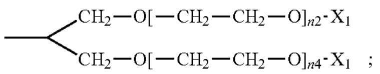

$R_3$ is hydrogen or $R_2$ and $R_3$ together form a fused ring, creating a core of Formula (V):

(V)

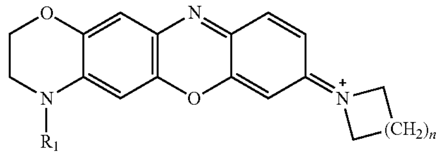

with the proviso that, when n is 1, and $R_3$ is H, $R_1$ and $R_2$, together with the nitrogen atom to which they are bound, may form a pyrrolidinyl ring;

$X_1$ in each instance is independently selected from $C_1$-$C_6$ straight or branched alkyl, $C_1$-$C_6$ straight or branched alkenyl, $C_1$-$C_6$ straight or branched alkynyl, and $-Si(C_1$-$C_4$ alkyl$)_3$; n is an integer selected from the group of 1 and 2;

n1 is an integer independently selected in each instance from the group of 1, 2, 3, and 4;

n2 is an integer independently selected in each instance from the group of 1, 2, 3, 4, 5, 6, 7, 8, 9, and 10;

n3 is an integer independently selected in each instance from the group of 1, 2, 3, 4, 5, 6, 7, 8, 9, and 10;

n4 is an integer independently selected in each instance from the group of 1, 2, 3, 4, 5, 6, 7, 8, 9, and 10; and with the proviso that the sum of n2+n2 is not greater than 10;

with the proviso that the sum of n2+n3 is not greater than 10;

with the proviso that the sum of n2+n4 is not greater than 10;

with the proviso that the sum of n3+n4 is not greater than 10; and with the proviso that, when n is 2, $R_1$ and $R_2$ are not both methyl, $R_1$ and $R_2$ are not both ethyl, $R_1$ and $R_2$ are not both n-propyl, $R_1$ and $R_2$ are not both n-butyl, and $R_1$ and $R_2$ are not both n-pentyl.

Within each of the specific embodiments herein, there is a further embodiment that provides a compound as defined by all variables and provisos for the specific embodiment in question, with the further proviso that none of the sum of n1+n2, the sum of n1+n3, and the sum of n1+n4 are greater than 10.

Within each of the specific embodiments herein, there is a further embodiment that provides a compound as defined by all variables and provisos for the specific embodiment in question, with the further proviso that none of the sum of n1+n2, the sum of n1+n3, and the sum of n1+n4 are greater than 8.

Within each of the specific embodiments herein, there is a further embodiment that provides a compound as defined by all variables and provisos for the specific embodiment in question, with the further proviso that none of the sum of n1+n2, the sum of n1+n3, and the sum of n1+n4 are greater than 6.

Within each of the specific embodiments herein, there is a further embodiment that provides a compound as defined by all variables and provisos for the specific embodiment in question, with the further proviso that none of the sum of n1+n2, the sum of n1+n3, and the sum of n1+n4 are greater than 4.

Within each of the specific embodiments herein, there is a further embodiment that provides a compound as defined by all variables and provisos for the specific embodiment in question, with the further proviso that none of the sums in the group of the sum of n1+n2, the sum of n1+n3, and the sum of n1+n4 are greater than 10.

Within each of the specific embodiments herein, there is a further embodiment that provides a compound as defined by all variables and provisos for the specific embodiment in question, with the further proviso that none of the sums in the group of the sum of n1+n2, the sum of n1+n3, and the sum of n1+n4 are greater than 8.

Within each of the specific embodiments herein, there is a further embodiment that provides a compound as defined by all variables and provisos for the specific embodiment in question, with the further proviso that none of the sums in the group of the sum of n1+n2, the sum of n1+n3, and the sum of n1+n4 are greater than 6.

Within each of the specific embodiments herein, there is a further embodiment that provides a compound as defined by all variables and provisos for the specific embodiment in question, with the further proviso that none of the sums in the group of the sum of n1+n2, the sum of n1+n3, and the sum of n1+n4 are greater than 4.

Two additional and separate embodiments provide, respectively, a compound of Formula (VI) and a compound of Formula (VII):

(VI)

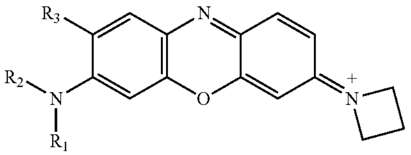

(VII)

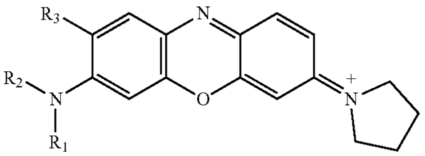

wherein all variables, including $R_1$, $R_2$, $R_3$, $X_1$, n, n1, n2, n3, and n4, along with all provisos, are as defined for Formula (I), above.

Two more separate embodiments provide, respectively, a compound of Formula (VI) and a compound of Formula (VII), wherein in each embodiment $R_3$ is H, and $R_1$ and $R_2$ are each independently selected from the group of methyl, ethyl, n-propyl, isopropyl, n-butyl, sec-butyl, and tert-butyl.

Two more separate embodiments provide, respectively, a compound of Formula (VI) and a compound of Formula (VII), wherein in each embodiment $R_3$ is H, and $R_1$ and $R_2$ are each independently selected from the group of methyl, ethyl, n-propyl, isopropyl, n-butyl, sec-butyl, and tert-butyl, with the proviso that $R_1$ and $R_2$ are not the same.

Two more separate embodiments provide, respectively, a compound of Formula (VI) and a compound of Formula (VII), wherein in each embodiment $R_3$ is H, and $R_1$ and $R_2$ are each independently selected from the group of methyl, ethyl, n-propyl, and isopropyl, with the proviso that $R_1$ and $R_2$ are not the same.

Two further separate embodiments provide, respectively, a compound of Formula (VI) and a compound of Formula (VII), wherein in each embodiment $R_3$ is H, and $R_1$ is selected from the group of methyl, ethyl, n-propyl, isopropyl, n-butyl, sec-butyl, and tert-butyl, and $R_2$ is selected from the group of $-(CH_2)_{n1}-SO_3$, $-(CH_2)_{n1}-N+(CH_3)_3$, $-CH_2-CH_2-O-X_1$, $-CH_2-CH_2-O-[CH_2-CH_2-O]_{n2}-X_1$, $-CH_2-CH_2-CH_2-O-X_1$, and $-CH_2-CH_2-CH_2-O-[CH_2-CH_2-CH_2-O]_{n3}-X_1$; or a moiety selected from the group of:

a)

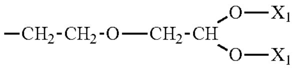

b)

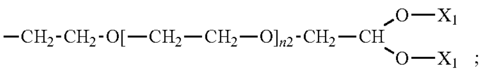

c)

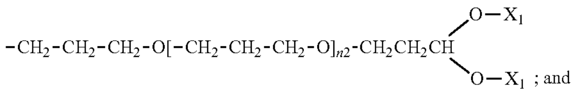

; and d)

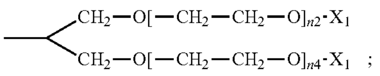

$X_1$ in each instance is independently selected from $C_1$-$C_6$ straight or branched alkyl, $C_1$-$C_6$ straight or branched alkenyl, $C_1$-$C_6$ straight or branched alkynyl, and $-Si(C_1$-$C_4$ alkyl$)_3$; n1 is an integer independently selected in each instance from the group of 1, 2, 3, and 4;

n2 is an integer independently selected in each instance from the group of 1, 2, 3, 4, 5, 6, 7, 8, 9, and 10;

n3 is an integer independently selected in each instance from the group of 1, 2, 3, 4, 5, 6, 7, 8, 9, and 10;

n4 is an integer independently selected in each instance from the group of 1, 2, 3, 4, 5, 6, 7, 8, 9, and 10; and with the proviso that the sum of n2+n4 when $R_2$ is the moiety represented by k), above, is not greater than 10.

A further embodiment comprises a compound of Formula (VIa):

(VIa)

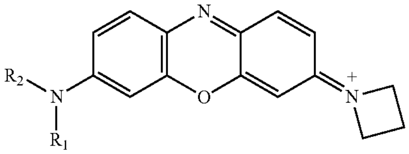

wherein $R_1$ and $R_2$ are selected independently from $C_1$-$C_6$ alkyl.

Another embodiment provides a compound of Formula (VIa), wherein $R_1$ and $R_2$ are each selected independently from $C_1$-$C_4$ alkyl.

Another embodiment provides a compound of Formula (VIa), wherein $R_1$ and $R_2$ are each selected independently from $C_1$-$C_3$ alkyl.

Another embodiment provides a compound of Formula (VIa), wherein $R_1$ is ethyl and $R_2$ is $C_1$-$C_4$ alkyl.

Another embodiment provides a compound of Formula (VIa), wherein $R_1$ is ethyl and $R_2$ is $C_1$-$C_3$ alkyl.

Another embodiment provides a compound of Formula (VIa), wherein $R_1$ is methyl and $R_2$ is $C_1$-$C_4$ alkyl.

Another embodiment provides a compound of Formula (VIa), wherein $R_1$ is methyl and $R_2$ is $C_1$-$C_3$ alkyl.

Another embodiment provides a compound of Formula (II):

(II)

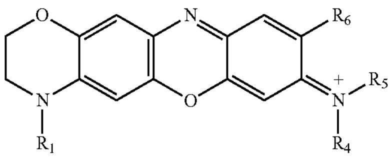

wherein $R_1$, $R_4$, $R_5$, $R_6$, and all associated variables and provisos are as defined for Formula (1), above.

An additional embodiment provides a compound of Formula (II), above, wherein $R_1$ is as defined above for Formula (1), $R_6$ is hydrogen, and $R_4$ and $R_5$ are each independently selected from the group of straight or branched $C_1$-$C_6$ alkyl, with the proviso that, when $R_1$ is methyl and $R_4$ is ethyl, $R_5$ is not ethyl.

A further embodiment provides a compound of Formula (VIII):

(VIII)

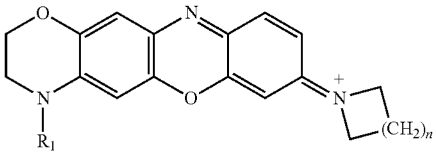

wherein n and $R_1$, along with all other associated variables and provisos, are as defined for Formula (1), above.

An additional embodiment provides a compound of Formula (VIIIa):

(VIIIa)

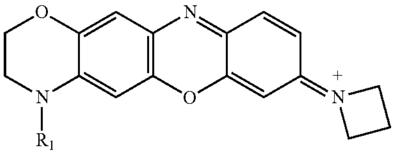

wherein $R_1$, along with all other associated variables and provisos, are as defined for Formula (1), above.

A further embodiment provides a compound of Formula (VIIIa), above, wherein $R_1$ is $C_1$-$C_4$alkyl.

Another embodiment provides a compound of Formula (VIIIa), above, wherein $R_1$ is $C_1$-$C_3$ alkyl.

An additional embodiment provides a compound of Formula (VIIIa), above, wherein $R_1$ is $C_1$-$C_2$ alkyl.

Another additional embodiment provides a compound of Formula (VIIIb):

(VIIIb)

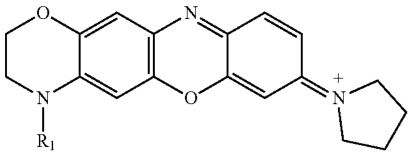

wherein $R_1$, along with all other associated variables and provisos, are as defined for Formula (1), above.

A further embodiment provides a compound of Formula (VIIIb), above, wherein $R_1$ is $C_1$-$C_4$ alkyl.

Another embodiment provides a compound of Formula (VIIIb), above, wherein $R_1$ is $C_1$-$C_3$ alkyl.

An additional embodiment provides a compound of Formula (VIIIb), above, wherein $R_1$ is $C_1$-$C_2$ alkyl.

A still further embodiment provides a compound of Formula (III):

(III)

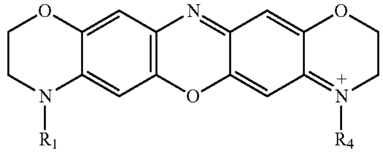

wherein $R_1$ and $R_4$, along with all associated variables and provisos, are as defined for Formula (1), above, with the proviso that, when $R_1$ is methyl, $R_4$ is not methyl, and with the proviso that, when $R_1$ is ethyl, $R_4$ is not ethyl.

Another embodiment provides a compound of Formula (III), above, wherein $R_1$ is $C_1$-$C_6$ alkyl, and $R_4$, along with all other associated variables and provisos, are as defined for Formula (1), above, and with the proviso that, when $R_1$ is methyl, $R_4$ is not methyl, and with the proviso that, when $R_1$ is ethyl, $R_4$ is not ethyl.

Still another embodiment provides a compound of Formula (III), above, wherein $R_1$ is $C_1$-$C_4$ alkyl, and $R_4$, along with all other associated variables and provisos, are as defined for Formula (1), above, and with the proviso that, when $R_1$ is methyl, $R_4$ is not methyl, and with the proviso that, when $R_1$ is ethyl, $R_4$ is not ethyl.

Still another embodiment provides a compound of Formula (III), above, wherein $R_1$ is $C_1$-$C_3$ alkyl, and $R_4$, along with all other associated variables and provisos, are as defined for Formula (1), above, and with the proviso that, when $R_1$ is methyl, $R_4$ is not methyl, and with the proviso that, when $R_1$ is ethyl, $R_4$ is not ethyl.

Still another embodiment provides a compound of Formula (III), above, wherein $R_1$ is $C_1$-$C_2$ alkyl, and $R_4$, along with all other associated variables and provisos, are as defined for Formula (1), above, and with the proviso that, when $R_1$ is methyl, $R_4$ is not methyl, and with the proviso that, when $R_1$ is ethyl, $R_4$ is not ethyl.

Yet another embodiment provides a compound of Formula (III), above, wherein $R_1$ and $R_2$ are each independently selected from $C_1$-$C_6$ alkyl, with the proviso that, when $R_1$ is methyl, $R_4$ is not methyl, and with the proviso that, when $R_1$ is ethyl, $R_4$ is not ethyl.

A further embodiment provides a compound of Formula (III), above, wherein $R_1$ and $R_2$ are each independently selected from $C_1$-$C_4$ alkyl, with the proviso that, when $R_1$ is methyl, $R_4$ is not methyl, and with the proviso that, when $R_1$ is ethyl, $R_4$ is not ethyl.

Another embodiment provides a compound of Formula (III), above, wherein $R_1$ and $R_2$ are each independently selected from $C_1$-$C_3$ alkyl, with the proviso that, when $R_1$ is methyl, $R_4$ is not methyl, and with the proviso that, when $R_1$ is ethyl, $R_4$ is not ethyl.

An additional embodiment provides a compound of formula (IX):

(IX)

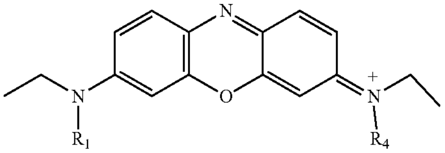

wherein $R_1$ and $R_4$ are each independently selected from $C_1$-$C_6$ alkyl.

A further embodiment provides a compound of formula (IX), wherein $R_1$ and $R_4$ are each independently selected from $C_1$-$C_4$ alkyl.

Another embodiment provides a compound of formula (IX), wherein $R_1$ and $R_4$ are each independently selected from $C_1$-$C_3$ alkyl.

A further embodiment provides a compound of formula (IX), wherein $R_1$ and $R_4$ are each independently selected from $C_1$-$C_2$ alkyl.

A further embodiment provides a compound of Formula (IX), wherein $R_1$ is as defined for Formula (I), above, along with all the defined associated variables and provisos.

Definitions

A "subject" or a "patient" refers to any animal. The animal may be a mammal. Examples of suitable mammals include human and non-human primates, dogs, cats, sheep, cows, pigs, horses, mice, rats, rabbits, and guinea pigs. In some embodiments the subject or patient is a human, particularly including a human undergoing or in need of a surgical procedure or examination.

The term "nerve" used herein means a bundle of neural axons. Within a nerve, each axon is surrounded by a layer of connective tissue called the endoneurium. The axons are bundled together into groups called fascicles, and each fascicle is wrapped in a layer of connective tissue called the perineurium. The entire nerve is wrapped in a layer of connective tissue called the epineurium. The term "nerve" is intended to include any tissues (e.g., the sinoatrial node or the atrioventricular node) or structures associated therewith (e.g., neuromuscular junctions).

The term "nerve-specific" or "nerve specific" herein refers to an agent that is drawn to a nerve or nerve tissue and may be used in fluorescent imaging techniques to help contrast and differentiate the nerve or nerve tissue from surrounding cells and/or tissues. The term "nerve specificity" refers to the nature or activity of an agent being nerve-specific.

The term "near infrared" or the acronym "(NIR)" refers to light at the near infrared spectrum, generally at a wavelength of about 0.65 to about 1.4 μm (700 nm-1400 nm. It may also refer to a range designated by the International Organization for Standardization as from a wavelength of about 0.78 μm to about 3 μm. In some embodiments, the preferred near infrared spectroscopy and imaging (NIRS) range is from about 650 nm to about 950 nm. In other embodiments, the preferred near infrared spectroscopy and imaging (NIRS) range is from about 650 nm to about 900 nm.

In some embodiments the agents and/or compositions comprising them are intended for direct/topical administration. Direct or topical administration are understood herein to comprise the administration of an agent or composition directly to surface of a tissue, organ, nerve bundle, or other bodily component. In some methods, the administration may be accomplished by brushing, spraying, or irrigation with the appropriate compound or composition.

In other embodiments, the agents and/or compositions may be administered systemically to the patient or subject, such as through intravenous injection or infusion.

In other embodiments, the agents and/or compositions may be administered locally to a desired tissue or organ, such as through injection.

The terms "effective amount" or "medically effective amount" or "imaging effective amount", or like terms refers to an amount of a compound or composition as described herein to cover a target area sufficiently to complete binding to one or more nerves such that they may be identified through relevant imaging techniques, particularly near-infrared imaging techniques.

The term "alkyl" refers to a straight or branched hydrocarbon. For example, an alkyl group can include those having 1 to 6 carbon atoms (i.e., $C_1$-$C_6$ alkyl or $C_{1-6}$ alkyl), 1 to 4 carbon atoms (i.e., $C_1$-$C_4$ alkyl or $C_1$-4 alkyl), 1 to 3 carbon atoms (i.e., $C_1$-$C_3$ alkyl or $C_1$-3 alkyl), or 1 to 2 carbon atoms (i.e., $C_1$-$C_2$ alkyl or $C_1$-2 alkyl). Examples of suitable alkyl groups include, but are not limited to, methyl, ethyl, n-propyl, isopropyl ($-CH(CH_3)_2$), 1-butyl (n-Bu, n-butyl, $-CH_2CH_2CH_2CH_3$), 2-methyl-1-propyl (i-Bu, i-butyl, $-CH_2CH(CH_3)_2$), 2-butyl (s-Bu, s-butyl, $-CH(CH_3)CH_2CH_3$), 2-methyl-2-propyl (t-Bu, t-butyl, $-C(CH_3)_3$), 1-pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), 1-hexyl ($-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl ($-C(CH_3)_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl ($-C(CH_3)(CH_2CH_3)_2$), 2-methyl-3-pentyl ($-CH(CH_2CH_3)CH(CH_3)_2$), 2,3-dimethyl-2-butyl ($-C(CH_3)_2CH(CH_3)_2$), and 3,3-dimethyl-2-butyl ($-CH(CH_3)C(CH_3)_3$).

The term "alkenyl" refers to a straight or branched hydrocarbon with at least one site of unsaturation, i.e. a carbon-carbon, $sp^2$ double bond. For example, an alkenyl group can have 2 to 4 carbon atoms (i.e., $C_2$-$C_4$ alkenyl). Examples of suitable $C_2$-$C_4$ alkenyl groups include, but are not limited to, ethenyl or vinyl ($-CH{=}CH_2$), allyl ($-CH_2CH{=}CH_2$), but-1-enyl ($-CH{=}CH-CH_2-CH_3$), but-2-enyl ($-CH_2-CH{=}CH-CH_3$), but-3-enyl ($-CH_2-CH_2-CH{=}CH$).

The term "alkynyl" refers to a straight or branched hydrocarbon with at least one site of unsaturation, i.e. a carbon-carbon, sp triple bond. For example, an alkynyl group can have 2 to 6 carbon atoms (i.e., $C_2$-$C_6$ alkyne), or 2 to 4 carbon atoms (i.e., $C_2$-$C_4$ alkynyl). Examples of suitable alkynyl groups include, but are not limited to, acetylenic ($-C-CH$), propargyl ($-CH_2C-CH$), and the like.

It is also understood that the compound structures generically and specifically described and/or shown herein include all corresponding resonance structures for such compounds. As an example using the structures below, while Compound A may be named 3-(dimethyl-14-azaneylidene)-7-(pyrrolidin-1-yl)-3H-phenoxazine and Compound B may be named N,N-dimethyl-7-(114-pyrrolidin-1-ylidene)-3H-715-phenoxazin-3-amine, each falls under the present definition of a compound of Formula (I) in which $R_1$ and $R_2$ form a pyrrolidinyl ring, $R_4$ and $R_5$ are each methyl, and $R_3$ and $R_6$ are both hydrogen, and each of compound structures A, B, C, and D include and represent the others herein.

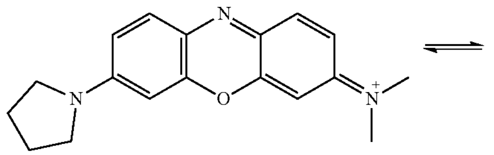

A

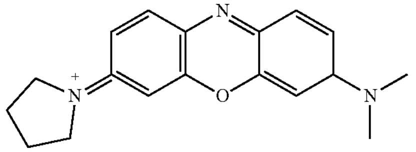

B

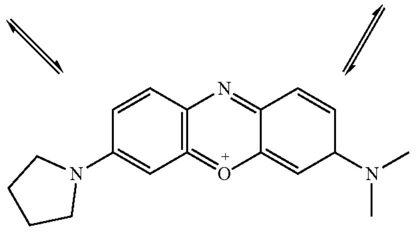

C

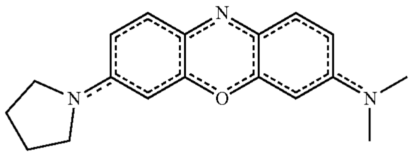

D

The term "imaging" herein refers to the use of fluorescent compounds in conventional medical imaging techniques including, but not limited to, those related to fluorescence image-guided surgery (including minimally invasive laparoscopy or endoscopy techniques), computer-assisted surgery or surgical navigation, radiosurgery or radiation therapy, interventional radiology, fluorescence microscopy, and laser-confocal microscopy. These techniques may include near infrared wavelengths from about 650 nm to 900 nm.

The term "label" refers to a molecule that facilitates the visualization and/or detection of a targeting molecule disclosed herein. In some embodiments, the label is a fluorescent moiety. The term "labeling" refers to a successful administration of the label to a target to allow such detection.

As used herein, the terms "robotic surgery", "robot-assisted surgery", or "computer-assisted surgery" refer to surgical techniques involving robotic systems that control the movement of medical instruments to conduct a surgical procedure with precise, flexible, and/or minimally invasive actions designed to limit the amount of surgical trauma, blood loss, pain, scarring, and post-surgical patient recovery time and/or complications, such as infection at the surgical area. Examples of robotic surgery include those conducted using the da Vinci Surgical System (Intuitive Surgical, Sunnyvale, CA, USA) approved by the U.S. Food and Drug Administration in 2000.

The terms "surgery" or "surgical method" as used herein, refers to any method used to manipulate, change, or cause an effect by a physical intervention. These methods include, but are not limited to open surgery, endoscopic surgery, laparoscopic surgery, minimally invasive surgery, robotic surgery, any procedures that may affect any neuron or nerve, such as placement of retractors during spinal surgery, electrically conducting cardiac tissue or nerve ablation, epidural injection, intrathecal injections, neuron or nerve blocks, implantation of devices such as neuron or nerve stimulators and implantation of pumps. These methods may also include biopsy or other invasive techniques for the collection of cell or tissue samples, such as for diagnostic purposes.

As used herein, the term "targeting molecule" refers to any agent (e.g., peptide, protein, nucleic acid polymer, aptamer, or small molecule) that associates with (e.g., binds to) a target of interest. The target of interest may be a nerve cell or an organ or tissue associated with one or more nerve cells or nerve structures. In some embodiments, the targeting molecule is any agent that associates with (e.g., binds to) a target comprising one or more neurons, nerves, or tissues or structures associated therewith, i.e. nerve tissues, nervous system tissues, nerve bundles, etc.

It is understood that nerve and nerve-related targets include those associated with the brain and spinal cord of the central nervous system (CNS) and the nerves of the peripheral nervous system (PNS).

The term "prostatectomy" refers to a surgical technique to remove all or part of a subject's prostate gland. A "radical prostatectomy" concerns removal of a subject's entire prostate gland, along with surrounding tissues, often including the seminal vesicles and nearby lymph nodes.

The terms "orthopedic limb repair" or "orthopedic limb repair surgeries" refer to surgical techniques performed on the limb musculoskeletal system of a subject. These techniques include limb reconstruction surgeries, joint replacement procedures, revision joint surgery, debridement, bone fusions, tendon or ligament repair, internal fixation of bone, and osteotomies.

The term "fluorophore" herein refers to any one of the compounds described herein for use in imaging techniques, particularly for nerve imaging techniques. Each of the compounds described herein as the product of a specific synthesis or described in a generic description is considered a fluorophore for methods, uses, and compositions.

The term "variable" or "variables" used in the generic descriptions and claims herein refer to the entities or moieties that may, in some instances, be chosen from a specified group. Such variables may include $R_1$, $R_2$, $R_3$, $R_4$, $R_5$, $R_6$, n1, n2, n3, n4, $X_1$, and the like.

All ranges disclosed and/or claimed herein are inclusive of the recited endpoint and independently combinable (for example, the ranges of "from 2 to 10" and "2-10" are inclusive of the endpoints, 2 and 10, and all the intermediate values). For example, a reference to "Claims 2-5" includes all claims 2, 3, 4, and 5.

The term "intraoperatively" as used in describing methods or uses herein refers to an activity that occurs during a surgical procedure or in immediate preparation for such procedure.

As used herein, terms "pharmaceutically acceptable" or "physiologically acceptable", and the like, used in regard to a formulation or composition component refer to a pharmaceutically acceptable vehicle that includes, without limitation, any and all carriers, solvents, dispersion media, coatings, antibacterial and antifungal agents, isotonic and absorption delaying agents and the like. Such materials provide an acceptable level of activity of the fluorophore/compound in question and are compatible with and substantially non-toxic to the cells, tissues, organs, etc. with which they contact. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "carrier" refers to an excipient or vehicle that includes without limitation diluents, disintegrants, precipitation inhibitors, surfactants, glidants, emulsifiers, buffers, stabilizers, lubricants, and the like with which the compound in question is administered. Carriers are generally described herein and also in "Remington's Pharmaceutical Sciences" by E. W. Martin.

It should be understood, however, that the carriers selected for the pharmaceutical compositions, and the amounts of such carriers in the composition, may vary depending on the method of formulation.

The term "diluent" generally refers to a substance that is used to dilute the compound of interest prior to delivery.

Methods of Use

Provided is a method of detecting nerves in a tissue or organ, the method comprising:

a) administering an effective amount of a composition comprising a fluorophore as described herein to the tissue or organ to form a stained tissue or a stained organ; and
b) imaging the stained tissue or stained organ, thereby detecting nerves intraoperatively in the stained tissue or stained organ.

Provided is a method of detecting nerves intraoperatively in a subject undergoing surgery, the method comprising:

c) administering an effective amount of a composition comprising a fluorophore as described herein to the subject before or during surgery to form a stained tissue; and
d) imaging the stained tissue undergoing surgery in the subject, thereby detecting nerves intraoperatively in the subject undergoing surgery.

Also provided is a method of detecting nerves intraoperatively in a subject undergoing a prostatectomy surgery, the method comprising:

e) administering an effective amount of a composition comprising a fluorophore as described herein to the subject before or during the prostatectomy surgery to form a stained tissue; and
f) imaging the stained tissue undergoing surgery in the subject, thereby detecting nerves intraoperatively in the subject undergoing prostatectomy surgery.

In one embodiment is provided a method of detecting cavernous nerves intraoperatively in a subject undergoing a prostatectomy surgery, the method comprising:

g) administering an effective amount of a composition comprising a fluorophore as described herein to the subject before or during the prostatectomy surgery to form a stained tissue; and
h) imaging the stained tissue undergoing surgery in the subject, thereby detecting cavernous nerves intraoperatively in the subject undergoing prostatectomy surgery.

For each of the methods herein concerning a prostatectomy surgery or procedure, there is another embodiment in which the surgery or procedure is a radical prostatectomy.

For each of the methods above and herein, there is an embodiment in which the composition comprising a fluorophore is administered to the subject systemically.

For each of the methods above and herein, there is an embodiment in which the composition comprising a fluorophore is administered to the subject directly or topically, i.e. through direct administration or topical administration.

Within each of the methods herein, there is a further embodiment in which the administration of an effective amount of a composition comprising a fluorophore as described herein to the subject before or during the prostatectomy surgery to form a stained tissue can be completed in fifteen minutes or less. In a still further embodiment, the administration of an effective amount of a composition comprising a fluorophore as described herein to the subject before or during the prostatectomy surgery to form a stained tissue can be completed in ten minutes or less.

Also provided herein are methods of imaging nervous tissue tumors (neoplasms), including Gliomas, such as gliomatosis cerebri, Oligoastrocytomas, Choroid plexus papillomas, Ependymomas, Astrocytomas (Pilocytic astrocytomas and Glioblastoma multiforme), Dysembryoplastic neuroepithelial tumors, Oligodendrogliomas, Medulloblastomas, and Primitive neuroectodermal tumors; Neuroepitheliomatous tumors, such as Ganglioneuromas, Neuroblastomas, Atypical teratoid rhabdoid tumors, Retinoblastomas, and Esthesioneuroblastomas; and Nerve Sheath Tumors, such as Neurofibromas (Neurofibrosarcomas and Neurofibromatosis), Schwannomas, Neurinomas, Acoustic neuromas, and Neuromas.

Provided is a method of imaging a target area in a subject, the method comprising contacting the target area in the subject with a compound selected from those herein and detecting the compound in the target using fluorescence or near-infrared imaging.

Also provided is a method of imaging one or more nerves in a target area in a subject, the method comprising contacting the target area in the subject with a compound selected from those herein and detecting the compound in the target using fluorescence imaging.

Also provided is a method of imaging one or more nerves in a target area in a subject, the method comprising contacting the target area in the subject with a compound selected from those herein and detecting the compound in the target using near-infrared imaging.

Also provided is a method of minimizing nerve damage in a target area in a subject during a medical procedure, the method comprising the steps of:

a) contacting the target area in the subject with a compound selected from those herein;

b) detecting one or more nerves bound by the compound in the target area using fluorescence imaging; and c) minimizing actions of the medical procedure that may damage one or more nerves detected.

The method above may be used to identify nerves and minimize damage to them that may be caused by a medical procedure, including traumatic, thermal, and radiological damage or that are caused by the application of therapeutic agents, anesthetics, or anesthesia in the target area.

In some embodiments, the medical procedure referenced in the method above is a surgical procedure. In other embodiments, the medical procedure is a biopsy procedure, a radiological procedure, or the application of anesthetic or anesthesia to the subject. In further embodiments, the medical procedure in the method above is the insertion or implantation of a medical device, including a medical pump, stent, pacemaker, port, artificial joints, valves, screws, pins, plates, rods, cosmetic implants, neurostimulators, and the like.

Also provided is the use of any compound disclosed herein in the preparation of a composition for use in imaging one or more nerves in a subject using from near-infrared imaging.

Nerve damage plagues surgical outcomes, significantly affecting post-surgical quality of life. Despite the practice of nerve sparing techniques for decades, intraoperative nerve identification and sparing remains difficult and success rates are strongly correlated with surgeon experience level and ability to master the technique (Walsh & Donker. The Journal of urology 128, 492-497 (1982); Ficarra et al. Eur Urol 62, 405-417 (2012); Damber & Khatami. Acta oncological 44, 599-604 (2005)). Fluorescence-guided surgery (FGS) shows promise for enhanced visualization of specifically highlighted tissue, such as nerves and tumor tissue, intraoperatively. FGS using optical imaging technology is capable of real-time, wide field identification of targeted tissues with high sensitivity and specificity from tissue targeted fluorescent probes. See, for instance: Frangioni. Journal of clinical oncology: official journal of the American Society of Clinical Oncology 26, 4012-4021 (2008); Gibbs. Quantitative imaging in medicine and surgery 2, 177-187 (2012); Gioux et al. Molecular imaging 9, 237-255 (2010); Vahrmeijer et al. Nature reviews. Clinical oncology 10, 507-518 (2013); and Nguyen et al. Nature reviews. Cancer 13, 653-662 (2013).[1,5] Operating in the near-infrared (NIR) optical window (650-900 nm wavelengths) where tissue chromophore absorbance, autofluorescence and scattering are minimal, FGS technologies have the ability to identify targeted tissues at millimeter to centimeter depths against a black background (Chance. Annals of the New York Academy of Sciences 838, 29-45 (1998); Gibbs. Quantitative imaging in medicine and surgery 2, 177-187 (2012)).

Several imaging systems have been developed for FGS applications. see, for instance: Lee et al. Plastic and reconstructive surgery 126, 1472-1481 (2010); Tummers et al. European journal of surgical oncology: the journal of the European Society of Surgical Oncology and the British Association of Surgical Oncology 40, 850-858 (2014); Troyan et al. Annals of surgical oncology 16, 2943-2952 (2009); Ashitate et al. Real-time simultaneous near-infrared fluorescence imaging of bile duct and arterial anatomy. The Journal of surgical research 176, 7-13 (2012); Verbeek et al. The Journal of urology 190, 574-579 (2013); Gibbs-Strauss et al. Molecular imaging 10, 91-101 (2011); Hirche et al. Surgical innovation 20, 516-523 (2013); Gotoh et al. Journal of surgical oncology 100, 75-79 (2009); and Kitagawa et al. Anticancer research 35, 6201-6205 (2015). Importantly, the da Vinci surgical robot, frequently used for robotic assisted radical prostatectomy (RP), can be equipped with an FDA approved fluorescence imaging channel.

Direct administration (also sometimes referred to as local administration) is an attractive alternative to systemic administration of fluorescent probes for minimizing potential toxicity and easing regulatory burdens for first in human clinical studies. By selectively labeling tissues within the surgical field, direct administration requires a significantly lower dose than systemic administration. A direct administration methodology has been developed that provides equivalent nerve signal to background (SBR) to systemic administration following a 15-minute staining protocol. Barth & Gibbs. Theranostics 7, 573-593 (2017). This methodology has been successfully applied to autonomic nerve models, which closely mimic the nerves surrounding the prostate. This method has additional benefits in the application to RP since nerve labeling via systemic administration during RP would generate high background from nerves in the prostate, which are not able to be spared, and renal fluorophore clearance, producing significant fluorescence signal in the urine within the adjacent bladder. Both of these extraneous fluorescence signals would diminish the ability to identify the cavernous nerves within the neurovascular bundle (NVB), which are responsible for continence and potency (Barth and Summer. Theranostics (2016). Tewari et al. BJU international 98, 314-323 (2006); Patel et al. Eur Urol 61, 571-576 (2012)). Perhaps most importantly, the direct administration methodology requires 16 times lower dose than systemic administration and when scaled to humans by body surface area the dose falls within the requirements for clinical translation under an exploratory investigational new drug (eIND) application to the FDA. Studies conducted under an eIND require minimal preclinical toxicity testing, since only a microdose (<100 μg) is administered to each patient, significantly reducing the cost of first-in-human studies.

While the direct administration methodology has provided high nerve specificity and SBR with a short staining protocol in preclinical rodent models (Barth & Gibbs. Theranostics 7, 573-593 (2017)), preliminary staining studies in large animal models generated significant background. To facilitate clinical translation, an improved formulation strategy that is FDA approved and facilitates increased application control for staining a variety of tissue surfaces, angles, and morphologies will be required.

Formulations comprising one or more of the compounds disclosed herein can be used to image nerves or nerve tissue. In particular embodiments, the formulations of the disclosure can be used to image nerves or nerve tissue in a subject. In particular embodiments, images of nerves can be obtained intraoperatively during FGS. In particular embodiments, the visualization of nerves during FGS allows surgery to be performed on tissue of interest while sparing nerves so as to reduce incidence of nerve injury during surgery. The area where surgery is performed or nearby regions can be surgically exposed. Surgery can be performed on organs, which include tissues such as nerve tissue, muscle tissue, and adipose tissue. The surgery can be laparoscopic, which is minimally invasive and includes the use of a thin, tubular device (laparoscope) that is inserted through a keyhole incision into a part of a subject's body, such as the abdomen or pelvis. The surgery can be assisted by a robot. Robot-assisted surgery can offer more precision, flexibility, and control, and is often associated with minimally invasive surgery.

In particular embodiments, the fluorophore concentration in a formulation that is directly applied to nerve tissue includes a concentration range of 40 to 300 μg/mL. In particular embodiments, the fluorophore concentration in a formulation for direct application includes 40 μg/mL, 50 μg/mL, 60 μg/mL, 70 μg/mL, 80 μg/mL, 90 μg/mL, 100 μg/mL, 110 μg/mL, 120 μg/mL, 130 μg/mL, 140 μg/mL, 150 μg/mL, 160 μg/mL, 170 μg/mL, 180 μg/mL, 190 μg/mL, and 200 μg/mL. In particular embodiments, the fluorophore concentration in a formulation for direct application is 50 μg/mL. In particular embodiments, the fluorophore concentration in a formulation for direct application is 200 μg/mL.

A formulation of the disclosure can be systemically applied to a subject for imaging of nerves. In particular embodiments, systemic application of a formulation includes intravenous injection of the formulation into a subject.

A formulation that is directly applied to a tissue can be allowed to penetrate the tissue for a given amount of time after direct application. In particular embodiments, the formulation can be allowed to penetrate the tissue for 30 seconds to 15 minutes, for 1 to 10 minutes, for 1 to 5 minutes, for 1 minute, for 2 minutes, for 3 minutes, for 4 minutes, or for 5 minutes. In particular embodiments, the formulation can be allowed to penetrate the tissue for 1 to 2 minutes. A formulation that is systemically applied to a subject can be administered a sufficient time before imaging such that the formulation can reach the area to be imaged and is present in such area at the time of imaging. In particular embodiments, a formulation that is systemically applied to a subject can be administered a sufficient time prior to imaging to allow uptake of the formulation by tissue in the subject. In particular embodiments, the formulation may be administered up to or less than 30 minutes, 1 hour, 2 hours, 3 hours, 4 hours, 5 hours, 6 hours, 7 hours, or 8 hours before imaging. The amount of time required may depend on the nerve imaging application and the administration site. In particular embodiments, the formulation is administered no more than 30 minutes, 1 hour, 2 hours, 3 hours, or 4 hours before imaging. In particular embodiments, the formulation is administered no more than 2 hours before imaging.

Tissue stained by a formulation including a fluorophore by direct application can be washed with buffer prior to imaging of the stained tissue. Washing of tissue stained by a formulation including a fluorophore can include flushing the tissue with an appropriate buffer and removing the buffer. In particular embodiments, the stained tissue can be washed 1 to 18 times, 1 to 10 times, 1 to 6 times, 1 time, 2 times, 3 times, 4 times, 5 times, or 6 times, with wash buffer.

In particular embodiments, the stained tissue can be washed 6 times. In particular embodiments, the wash buffer is phosphate-buffered saline (PBS). In particular embodiments, washing the stained tissue removes unbound fluorophore. In particular embodiments, washing the stained tissue increases the nerve signal intensity and/or the signal to background ratio (SBR) as compared to no washing of the stained tissue. In particular embodiments, washing the stained tissue resolubilizes the fluorophore and allows for further diffusion of the fluorophore into the nerve tissue.

Imaging a tissue stained by a formulation including a fluorophore includes applying light to tissue that has been stained with a formulation of the disclosure. The light can be at a wavelength sufficient to excite the fluorophore in the formulation to fluoresce. In particular embodiments, light to excite the fluorophore is at a wavelength in the near infrared spectra. In particular embodiments, the fluorophore of a formulation emits at a wavelength in the near infrared spectra. In particular embodiments, the near infrared spectra includes a wavelength of 650 to 900 nm. In some embodiments, the infrared spectrum of interest is about 700 nm. In other embodiments, the infrared spectra of interest includes a wavelength of from about 725 nm to about 875 nm.

Imaging a tissue stained by a formulation including a fluorophore includes obtaining fluorescence images of the stained tissue by optical imaging systems such as ones described in the Examples.

In particular embodiments, imaging a tissue includes observing fluorescence images of the stained tissue. The fluorescence images can include still images (whether printed or on screen), or real-time images on a video monitor. In particular embodiments, the individual images of nerves obtained by staining of the nerves with the present formulations can be used for diagnostic purposes and for documentation of nerve location. By observing the fluorescence images the surgical team can determine the absence or presence of a nerve in the image. The surgical team can thus use information about the presence/absence or location of one or more nerves to determine how they will perform the surgical procedure. For example, based on information obtained through the disclosed methods, the surgical team may decide to perform a surgical cut at a point in the tissue where they are less likely to inadvertently cut or surgically contact a particular nerve based on the perceived absence of a nerve in an area of the tissue.

The information obtained from the obtained image can aid in grafting the ends of the nerves if they are transected. In the event of transection, nerve grafts can be applied directly to the ends to facilitate sprouting of regenerative neural fibers. In this case, the light visible from the fluorescence of the ends of transected nerves provides a target to guide the anastomosis of the nerves by the nerve graft.

Provided is a formulation comprising an effective amount of a compound as described herein and a pharmaceutically or physiologically acceptable carrier. In some embodiments the pharmaceutically or physiologically acceptable carrier is an aqueous carrier.

Aqueous carriers may include saline solutions, such as buffered saline solutions, as well as aqueous dextrose and glycerol solutions. Suitable pharmaceutical carriers may also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents (such as the KOLLIPHOR® family of products available from BASF), or pH buffering agents.

Formulations of the present disclosure to detect nerve tissue can also be provided as kits.

Kits for detecting nerve tissue can include, in different containers: (i) a water-based formulation comprising a fluorophore, and (ii) one or more wash buffers. Kits can also include a notice in the form prescribed by a governmental agency regulating the manufacture, use, or sale of pharmaceuticals or biological products, which notice reflects approval by the agency of manufacture, use, or sale for human administration. The notice may state that the provided active ingredients can be administered to a subject. The kits can include further instructions for using the kit, for example, instructions regarding: directly applying the formulations to a tissue; washing to remove excess formulation; systemically administering the formulations to a subject; applying light for visualization of the fluorophores; capturing fluorescent images of the tissue; proper disposal of related waste; and the like. The instructions can be in the form of printed instructions provided within the kit or the instructions can be printed on a portion of the kit itself. Instructions may be in the form of a sheet, pamphlet, brochure, CD-ROM, or computer-readable device, or can provide directions to instructions at a remote location, such as a website. In particular embodiments, kits can also include some or all of the necessary laboratory and/or medical supplies needed to use the kit effectively, such as syringes, ampules, tubing, gloves, tubes, buffers, and the like. Variations in contents of any of the kits described herein can be made.

General

All reagents were purchased from Sigma Aldrich, Fisher Scientific, or TCI. Unless otherwise indicated, all commercially available starting materials were used directly without further purification. Analytical TLC was performed on Millipore ready-to-use plates with silica gel 60 (F254, 32-63 m). Purification was performed on a Biotage Isolera Flash System using pre-packed silica gel cartridges or on a reverse phase preparative HPLC (Agilent 1250 Infinity HPLC).

LCMS Characterization

Mass-to-charge ratio and purity of the Oxazine compounds were characterized on an Agilent 6244 time-of-flight LCMS with diode array detector VL+. Sample (10 µL) was injected into a C18 column (Poroshell 120, 4.6×50 mm, 2.7 micron), and eluted with a solvent system of A ($H_2O$, 0.1% FA) and B (MeCN, 0.1% FA) at 0.4 mL/min, from A/B=90/10 to 5/95 over 10 min, maintained at A/B=5/95 for additional 5 min. Ions were detected in positive ion mode by setting the capillary voltage at 4 kV and gas temperature at 350° C.

Nerve-Specificity Screening Using Direct/Topical Administration

Each compound was screened for its tissue-specificity using a previously published direct/topical administration strategy in murine brachial plexus and sciatic nerves.[6] Each compound from the Oxazine library was formulated in the previously utilized co-solvent formulation (10% DMSO, 5% KOLLIPHOR®, 65% serum and 20% phosphate buffered saline) at 125 µM. 100 µL of the formulated Oxazine were incubated on the exposed brachial plexus or sciatic nerve for 5 minutes. The fluorophore containing solution was removed and the area was irrigated with saline 18 times to remove any unbound fluorophore. Co-registered fluorescence and color images were collected of each stained area 30 minutes after Oxazine direct/topical administration using a custom built macroscopic imaging system with 620/60 nm excitation and 700/75 nm bandpass emission filters. Custom written MatLab code was used to analyze the tissue specific fluorescence where regions of interest were selected on the nerve, muscle and adipose tissue using the white light images. These regions of interest were then analyzed on the co-registered matched fluorescence images permitting assessment of the nerve to muscle and nerve to adipose ratios.

Nerve-Specificity Screening Using Systemic Administration

Each compound was screened for its tissue-specificity using a previously published systemic administration strategy in murine brachial plexus and sciatic nerves.[6] Each compound from the Oxazine library was formulated in the previously utilized co-solvent formulation (10% DMSO, 5% KOLLIPHOR®, 65% serum and 20% phosphate buffered saline) at 2 mM. 100 µL of the formulated Oxazine were administered intravenously 4 hours before exposing the brachial plexus and sciatic nerves. Co-registered fluorescence and color images were collected of each nerve site using a custom built macroscopic imaging system with 620/60 nm excitation and 700/75 nm bandpass emission filters. Custom written MatLab code was used to analyze the tissue specific fluorescence where regions of interest were selected on the nerve, muscle and adipose tissue using the white light images. These regions of interest were then analyzed on the co-registered matched fluorescence images permitting assessment of the nerve to muscle and nerve to adipose ratios in blinded manner.

Chemical Synthesis

Scheme: Synthetic route to LGW11-98.

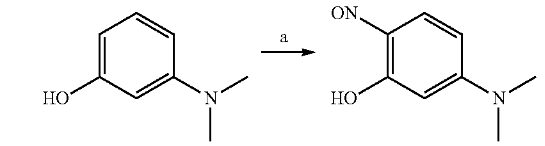

1 2

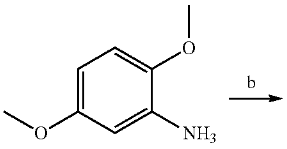

3

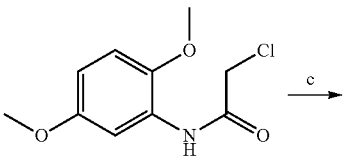

4

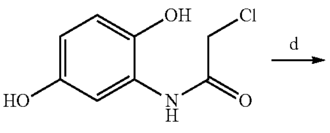

5

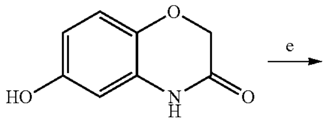

6

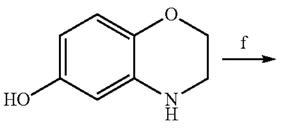

7

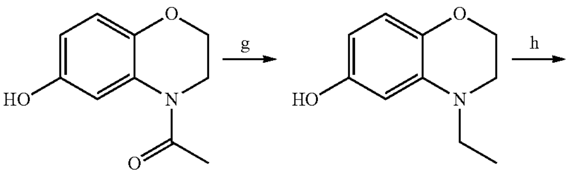

8 9

-continued

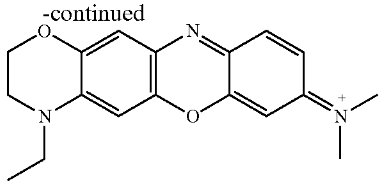

LGW11-98

Reagents and conditions: a) 6M HCl, $NaNO_2$, 0° C.; b) Chloroacetic chloride, TBAB, $NaHCO_3$, $H_2O$, 0° C.; c) 1M BBr3, DCM, 0° C. to rt; d) NaH, THF, 0° C. to rt; e) $BH_3$—THF, 0° C. to rt; f) $Ac_2O$, $H_2O$, 50° C. to rt; g) $BH_3$—THF, THF, 0° C. to rt; h) compound 2, $HClO_4$, 90% iPrOH, 80° C.

5-(dimethylamino)-2-nitrosophenol (2): Compound 1 (1.00 g, 7.29 mmol) was dissolved in an ice-cold 6 M HCl solution (5 mL). To the solution above, $NaNO_2$ (0.513 g, 7.44 mmol) was added portion wise over 1 h while maintaining the temperature of the solution below 5° C., such that no brown NOx vapors were observed. The reaction mixture was stirred for additional 2 h. After which, the precipitate was filtered through a Buchner funnel and washed with small portions of ice-cold 2 M HCl solution. The product was left in the funnel and air dried overnight to afford compound 2 (1.01 g, 84%) as a yellow solid, which was used for the next step without further purification.

2-chloro-N-(2,5-dimethoxyphenyl)acetamide (4): Compound 3 (20.0 g, 130 mmol) was dissolved in anhydrous MeCN (60 mL) under $N_2$, and chilled in an ice bath. To the solution, $Et_3N$ (40 mL, 287 mmol) and Chloroacetic chloride (12.7 mL, 159 mmol) were carefully added. The reaction mixture was stirred for 1 h, then diluted with 500 mL DI water. The solid suspension was filtered off to yield compound 4 (21.0 g, 70%) as a light brown solid, which was used for the next step without further purification.

2-chloro-N-(2,5-dihydroxyphenyl)acetamide (5): Compound 4 (10.0 g, 43.5 mmol) was dissolved in anhydrous DCM (20 mL) under $N_2$, and chilled in an ice bath. To the solution above, was added $BBr_3$(1 M in DCM, 130 mL, 130 mmol) dropwise over 1 h using a syringe pump. The reaction mixture was slowly warmed up to rt and stirred overnight. The reaction flask was placed in an ice bath, after sufficient amount of time for cooling, water was carefully added to the reaction mixture to destroy excess $BBr_3$. The resulting precipitate was collected via vacuum filtration and washed with small portions of DI water. The product was left in the funnel and air dried overnight to afford compound 5 (7.96 g, 91%), which was used for the next step without further purification.

6-hydroxy-2H+benzo[b][1,4]oxazin-3(4H)-one (6): Compound 5 (6.00 g, 29.8 mmol) was dissolved in anhydrous THF (50 mL) under $N_2$, and chilled in an ice bath. After sufficient time for cooling, NaH (60%, 4.17 g, 104 mmol) was added to the solution in 4 portions over 10 mins. The reaction mixture was slowly warmed to rt and stirred overnight. Upon the completion of the reaction, ice-cold water was carefully added to the reaction flask to destroy excess NaH. The reaction mixture was acidified with 2 M HCl, followed by extraction with EtOAc (5×100 mL). The combined organic layers were rinsed with brine and dried over anhydrous $Na_2SO_4$. The solvent was removed using a rotary evaporator and the residue was purified by flash column chromatography with silica gel, using EtOAc/DCM/Hexane as eluent to give compound 6 (3.12 g, 63%) as a light brown solid.

3,4-dihydro-21-benzo[b][1,4]oxazin-6-ol (7): A solution of 6 (2.2 g, 13.3 mmol) in anhydrous THF (40 mL) was stirred in an ice bath under $N_2$ for 30 mins. Borane tetrahydrofuran complex solution (1 M, 40 mL) was added to the solution above using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, the residue was purified by flash column chromatography with silica gel, using ErOAc/Hexane as eluent to obtain 7 (1.91 g, 95%).

1-(6-hydroxy-2,3-dihydro-4H-benzo[b][1,4]oxazin-4-yl)ethan-1-one (8): Compound 7 (1.00 g, 6.62 mmol) was suspended in 10 mL DI water, to which Acetic anhydride (2.5 mL, 26.5 mmol) was added dropwise. The reaction mixture was placed in an ultrasonication bath for 1 min, then was stirred in a water bath (50° C.) for 10 min. The resulting solution was stirred overnight at rt. After which, the solid was collected via vacuum filtration and washed with small portions of DI water. The product was left in the funnel and air dried overnight to afford compound 8 (1.21 g, 95%) as a white solid, which was used for the next step without further purification.

4-ethyl-3,4-dihydro-2H-benzo[b][1,4]oxazin-6-ol (9): A solution of 8 (900 mg, 10.0 mmol) in anhydrous THF (14 mL) was stirred in an ice bath under $N_2$ for 30 mins. Borane tetrahydrofuran complex solution (1 M, 14 mL) was added to the solution using a syringe pump over 30 mins, while maintaining the temperature of the solution below 5° C. The resulting reaction mixture was left in the ice bath and slowly warm to rt. After 24 h, the solution was placed in an ice bath again, and excess borane reagent was destroyed by carefully adding MeOH until no gas evolved. The solvent was evaporated under reduced pressure, the residue was purified by flash column chromatography with silica gel, using DCM/Hexane as eluent to give 9 (756 mg, 91%) as brown oil.

N-(4-ethyl-3,4-dihydro-[1,4]oxazino[2,3-b]phenoxazin-8(2H)-ylidene)-N-methylmethanaminium (LGW11-98): Compound 9 (40 mg, 0.22 mmol) was dissolved in a solution of i-PrOH/$H_2O$ (9/1, 3 mL) at 80° C. for 30 min. Compound 2 (73 mg, 0.22 mmol) was added to the solution in 5 portions over 15 mins. Then the reaction mixture was treated with $HClO_4$ (70%, 20 μL). The resulting solution was stirred overnight. The dark blue solution was evaporated under reduced pressure, and the residue was purified by flash column chromatography with silica gel, using a mobile phase of $CHCl_3$ and MeOH containing 0.5% formic acid (linear gradient, 2-15% of MeOH in $CHCl_3$). The fractions containing product were pooled and evaporated, affording LGW11-98 (26 mg, 38%) as a dark blue solid. MS(ESI): calcd for $C_{18}H_{200}N_3O_2$ [M]+310.1550; found 310.1563.

Scheme: Synthetic route to LGW13-79.

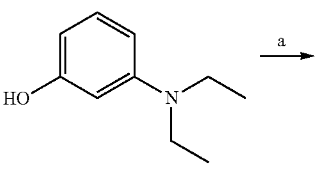

10

-continued

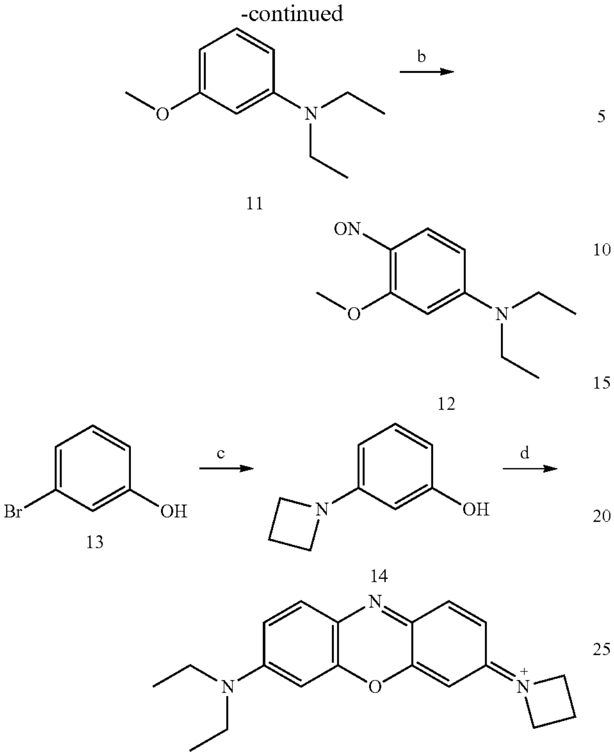

11

12

13

14

LGW13-79

Reagents and conditions: a) MeI, NaH, THF, 0° C. to rt; b) 2M HCl, $NaNO_2$, 0° C.; ii) $K_2CO_3$, 0° C.; c) $Pd(OAc)_2$, Verkade base, LiHMDS, azetidine, toluene, 80° C. d) compound 12, $HClO_4$, 90% i-PrOH, 80° C.

N,N-diethyl-3-methoxyaniline (11): Compound 10 (5.00 g, 30.3 mmol) was dissolved in anhydrous THF (50 mL) under $N_2$ and chilled in an ice bath for 30 mins. NaH (60%, 3.63 g, 90.8 mmol) was added to the solution in 3 portions over 10 mins while the temperature was kept below 5° C. After 10 mins, MeI (7.54 mL, 121 mmol) was added into the reaction mixture in one portion. The resulting suspension was slowly warmed up to rt and stirred overnight. Upon completion, DI water was added to the reaction mixture to destroy excess NaH. Organic solvent was removed under reduced pressure and the residue was extracted with DCM (3×100 mL). The combined organic layers were rinsed with brine, dried over anhydrous $Na_2SO_4$, and the solvent was removed using a rotary evaporator. The residue was purified by flash column chromatography with silica gel, using DCM/Hexane as eluent to give compound 11 (4.70 g, 88%) as clear oil.

N,N-diethyl-3-methoxy-4-nitrosoaniline (12): Compound 11 (1.08 g, 6.02 mmol) was dissolved in an ice-cold 2 M HCl solution (15 mL). To the solution above, $NaNO_2$ (457 mg, 6.63 mmol) was added portion wise over 1 h while maintaining the temperature of the solution below 5° C., such that no brown NOx vapors were observed. The reaction mixture was stirred for an additional 2 h. The solution was carefully basified with solid $K_2CO_3$ until pH value of the solution rose above 8. After which, the precipitate was filtered through a Buchner funnel and washed with small portions of DI water. The product was left in the funnel and air dried overnight to afford compound 12 (1.05 g, 84%) as a green solid, which was used for the next step without further purification.

3-(azetidin-1-yl)phenol (14): Compound 14 was synthesized following a slightly modified protocol published by Grimm et al.[7] An oven-dried flask was charged with $Pd(OAc)_2$ (52 mg, 0.231 mmol). The flask was sealed, evacuated under vacuum and backfilled 5 times with $N_2$ before toluene (40 mL) was added. A solution of compound 13 (2.00 g, 11.6 mmol) in toluene (10 mL), 2,8,9-triisobutyl-2,5,8,9-tetraaza-1-phosphabicyclo[3.3.3]undecane (159 mg, 0.463 mmol) in toluene (10 mL), and LiHMDS solution (1.3 M, 20 mL, 26 mmol) were then added sequentially. Following the addition of azetidine (792 mg, 13.9 mmol), the reaction was stirred at 80° C. overnight. It was then cooled to room temperature, deposited onto Celite, and concentrated to dryness. Purification by silica gel flash chromatography using a mobile phase of EtOAc and Hexanes provided compound 14 (1.38 g, 80%) as an off-white solid.

1-(7-(diethylamino)-3H-phenoxazin-3-ylidene)azetidin-1-ium (LGW13-79): Compound 14 (40 mg, 0.268 mmol) was dissolved in a solution of i-PrOH/$H_2O$ (9/1, 4 mL) at 80° C. for 30 min. Compound 12 (56 mg, 0.268 mmol) was added to the solution in 5 portions over 15 mins. Then the reaction mixture was treated with $HClO_4$ (70%, 20 µL). The resulting solution was stirred overnight. The dark blue solution was Then cooled to room temperature, evaporated under reduced pressure, and the residue was purified by flash column chromatography with silica gel, using a mobile phase of $CHCl_3$ and MeOH containing 0.5% formic acid (linear gradient, 2-15% of MeOH in $CHCl_3$). The fractions containing product were pooled and evaporated, affording LGW13-79 (25 mg, 30%) as a dark blue solid. MS(ESI): calcd for $C_{19}H_{22}N_3O$ [M]+308.1757; found 308.1763.

Scheme: Synthetic route to LGW14-42.

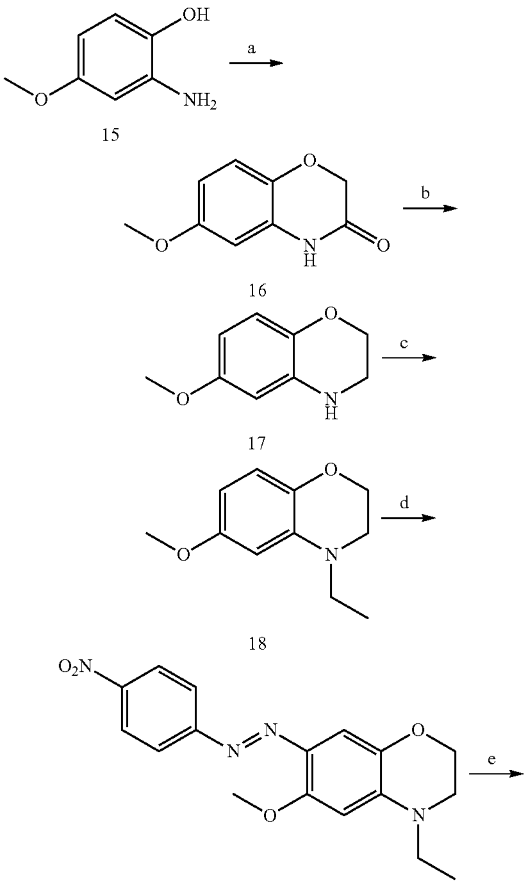

15

16

17

18

19

-continued

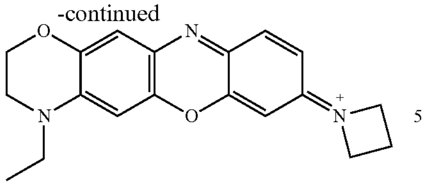

LGW14-42

Reagents and condtions: a) Chloroacetic chloride, $K_2CO_3$, MeCN, 80° C.; b) $BH_3$—THF, THF, 0° C. to rt; c) EtI, $Na_2CO_3$, MeCN, 80° C.; d) i) 2M HCl, p-nitrobenzenediazonium tetrafluoroborate, 0° C.; ii) $K_2CO_3$, 0° C.; e) compound 14, PPSE, $CF_3CH_2OH$, 80° C.

6-methoxy-2H-benzo[b][1,4]oxazin-3(4H)-one (16): Compound 16 was synthesized following a slightly modified protocol reported by Zhang et al.[8] Under $N_2$ atmosphere, compound 15 (2.00 g, 14.4 mmol) was dissolved in anhydrous MeCN (20 mL), to which 2-chloroacetyl chloride (1.37 mL, 17.3 mmol) was added dropwise. Following the addition of $K_2CO_3$ (4.97 g, 25.9 mmol), the reaction mixture was heated to 80° C. and stirred overnight. It was then cooled to room temperature, diluted with DCM, and filtered through Celite. The solvent was removed in vacuo, and the residue was purified by silica gel flash chromatography using a mobile phase of EtOAc and Hexanes, provided compound 16 (2.21 g, 86%) as a brown solid.

6-methoxy-3,4-dihydro-2H-benzo[b][1,4]oxazine (17): A solution of compound 16 (2.00 g, 11.2 mmol) in anhydrous THF (30 mL) was stirred in an ice bath under $N_2$ for 30 mins. Borane tetrahydrofuran complex solution (1 M, 30 mL) was added to the solution above dropwise over 30 mins using a syringe pump, while the temperature of the solution was maintained below 5° C. The resulting reaction mixture was left to stir in the ice bath and slowly warm to rt. After 24 h, the solution was placed in an ice bath again and excess borane reagent was destroyed by carefully adding MeOH until no gas evolved. The solvent was evaporated under reduced pressure and the residue was purified by flash column chromatography with silica gel, using DCM/Hexane as eluent, providing compound 17 (1.62 g, 88%) as a light pink solid.

4-ethyl-6-methoxy-3,4-dihydro-2H-benzo[b][1,4]oxazine (18): To a suspension of compound 17 (1.00 g, 6.05 mmol) and $Na_2CO_3$ (1.28 g, 12.1 mmol) in anhydrous MeCN (10 mL) under $N_2$ was added EtI (0.501 mL, 6.17 mmol) at rt. The reaction mixture was heated to 80° C. and stirred overnight. It was then cooled to room temperature, diluted with DCM, and filtered through Celite. The solvent was removed in vacuo, and the residue was purified by silica gel flash chromatography with silica gel, using DCM/Hexane as eluent to give compound 18 (1.01 g, 86%) as a light brown oil.

(E)-4-ethyl-6-methoxy-7-((4-nitrophenyl)diazenyl)-3,4-dihydro-2H-benzo[b][1,4]oxazine (19): Compound 18 (400 mg, 2.07 mmol) was dissolved in MeOH (1 mL). The solution was chilled in an ice bath, then treated with HCl (2 M, 10 mL). After 15 mins, p-nitrobenzenediazonium tetrafluoroborate (515 mg, 2.17 mmol) was added to the solution in 3 portions over an additional 15 mins, then stirred at 0° C. for 1 h. During this time, the color of the reaction mixture changed from orange to dark red. After two hours, the solution was carefully neutralized with solid $K_2CO_3$ until the pH value of the solution had risen above 7. The precipitate was collected via vacuum filtration and washed with small portions of DI water. The product was left in the funnel, air dried overnight, afforded compound 19 (537 mg, 76%) as a green solid, and used for the next step without further purification.

1-(4-ethyl-3,4-dihydro-[1,4]oxazino[2,3-b]phenoxazin-8(2H)-ylidene)azetidin-1-ium (LGW14-42): Compounds 14 (30 mg, 0.201 mmol) and 19 (69 mg, 0.201 mmol) were dissolved in a solution of trifluoroethanol (3 mL) containing Trimethylsilyl polyphosphate (30 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{19}H_{20}N_3O_2$ [M]+322.1550; found 322.1584.

Scheme: LGW14-45 synthesis.

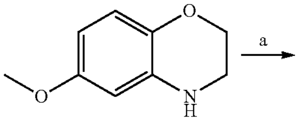

17

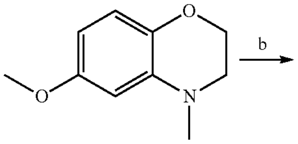

20

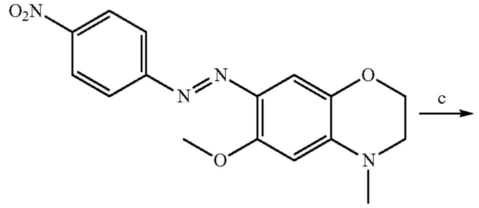

21

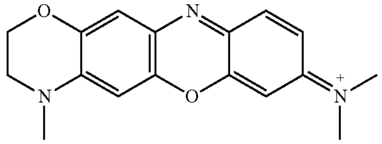

LGW14-45

Reagents and conditions: a) MeI, $Na_2CO_3$, MeCN, 80° C.; b) i) 2M HCl, p-nitrobenzenediazonium tetrafluoroborate, 0° C.; ii) $K_2CO_3$, 0° C.; c) compound 1, PPSE, $CF_3CH_2OH$, 80° C.

6-methoxy-4-methyl-3,4-dihydro-2H-benzo[b][1,4]oxazine (20): To a suspension of compound 17 (1.00 g, 6.05 mmol) and $Na_2CO_3$ (1.28 g, 12.1 mmol) in anhydrous MeCN (10 ml) under $N_2$ was added MeI (400 μL, 6. 36 mmol) at rt. The reaction mixture was heated to 80° C. and stirred overnight. It was then cooled to room temperature, diluted with DCM, and filtered through Celite. The solvent was removed in vacuo, and the residue was purified by silica gel flash chromatography with silica gel, using DCM/Hexane as eluent to give compound 20 (0.814 g, 75%) as a burgundy oil.

(E)-6-methoxy-4-methyl-7-((4-nitrophenyl)diazenyl)-3,4-dihydro-2H-benzo[b][1,4]oxazine (21): Compound 20 (400 mg, 2.23 mmol) was dissolved in MeOH (1 mL). The solution was chilled in an ice bath, then treated with HCl (2 M, 10 mL). After 15 mins, p-nitrobenzenediazonium tetrafluoroborate (555 mg, 2.34 mmol) was added to the solution in 3 portions over an additional 15 mins, then stirred at 0° C. for 1 h. During this time, the color of the reaction mixture changed from orange to dark red. After two hours, the solution was carefully neutralized with solid $K_2CO_3$ until the pH value of the solution had risen above 7. The precipitate was collected via vacuum filtration and washed with small portions of DI water. The product was left in the funnel, air dried overnight, afforded compound 21 (693 mg, 95%) as a dark red solid, and used for the next step without further purification.

N-methyl-N-(4-methyl-3,4-dihydro-[1,4]oxazino[2,3-b]phenoxazin-8(2H-ylidene)methanaminium (LGW14-45): Compounds 1 (30 mg, 0.219 mmol) and 21 (72 mg, 0.219 mmol) were dissolved in a solution of trifluoroethanol (3 mL) containing Trimethylsilyl polyphosphate (30 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{17}H_{18}N_3O_2$ [M]+296.1394; found 296.1441.

Scheme: Synthesis route to LGW14-46.

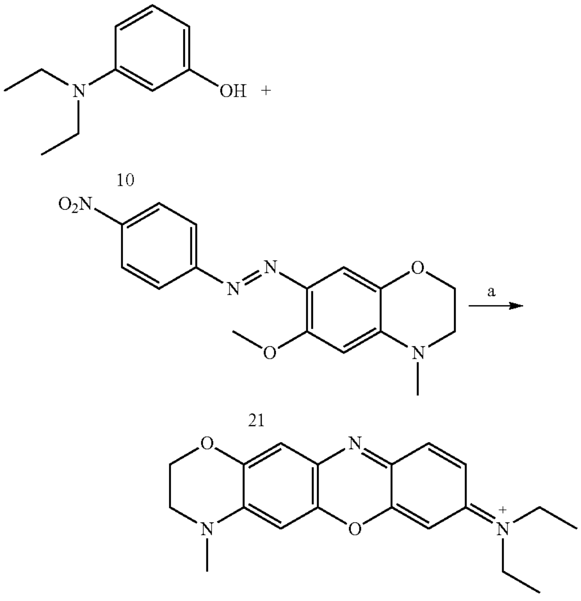

10

21

LGW14-46

Reagents and conditions: a) PPSE, $CF_3CH_2OH$, 80° C.

N-ethyl-N-(4-methyl-3,4-dihydro-[1,4]oxazino[2,3-b]phenoxazin-8(2H)-ylidene)ethanaminium (LGW14-46): Compounds 10 (30 mg, 0.182 mmol) and 21 (60 mg, 0.182 mmol) were dissolved in a solution of trifluoroethanol (3 mL) containing Trimethylsilyl polyphosphate (30 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{19}H_{22}N_3O_2$ $[M]^+$ 324.1707; found 324.1746.

Scheme: Synthetic route to LGW14-47.

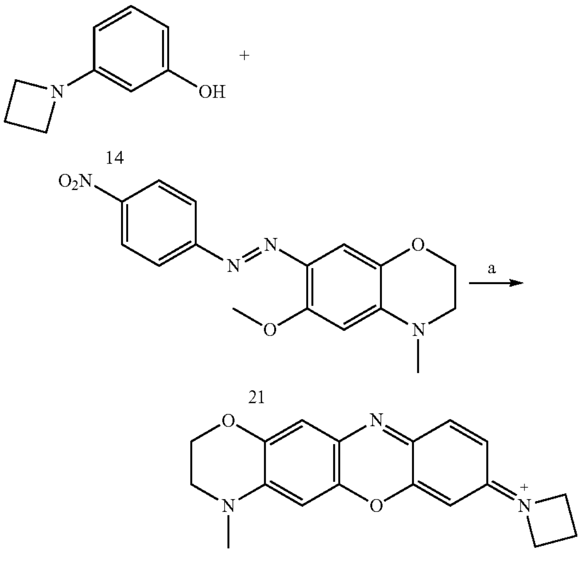

14

21

LGW14-47

Reagents and conditions: a) PPSE, $CF_3CH_2OH$, 80° C.

1-(4-methyl-3,4-dihydro-[1,4]oxazino[2,3-b]phenoxazin-8(2H)-ylidene)azetidin-1-ium (LGW14-47): Compounds 14 (30 mg, 0.201 mmol) and 21 (66 mg, 0.201 mmol) were dissolved in a solution of trifluoroethanol (3 mL) containing Trimethylsilyl polyphosphate (30 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{18}H_{18}N_3O_2$ [M]+308.1394; found 308.1436.

Scheme: Synthetic route to LGW14-49.

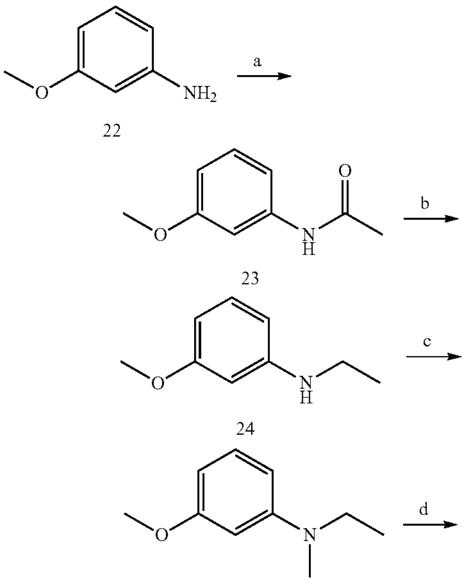

22

23

24

25

-continued

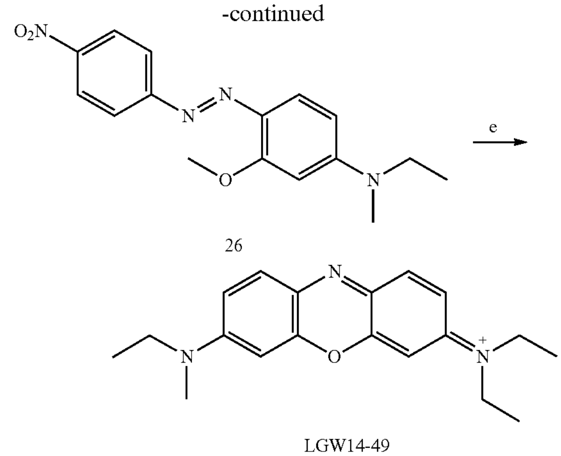

26

LGW14-49

Reagents and conditions: a) $Ac_2O$, $H_2O$, 50° C. to rt; b) $BH_3$—THF, THF, 0° C. to rt; c) MeI, $Na_2CO_3$, MeCN, 80° C.; d) i) 2M HCl, p-nitrobenzenediazonium tetrafluoroborate, 0° C.; ii) $K_2CO_3$, 0° C.; e) compound 10, PPSE, $CF_3CH_2OH$, 80° C.

N-(3-methoxyphenyl)acetamide (23): Compound 22 (2.00 g, 16.2 mmol) was suspended in 20 mL DI water, to which acetic anhydride (4.61 mL, 48.7 mmol) was added dropwise. The reaction mixture was placed in an ultrasonication bath for 1 min, then stirred in a heated water bath (50° C.) for 10 min. The resulting solution was stirred overnight at rt. The solid product was collected via vacuum filtration and washed with small portions of DI water. The product was left in the funnel, air dried overnight, provided compound 23 (2.37 g, 88%) as an off-white solid, and used for the next step without further purification.

N-ethyl-3-methoxyaniline (24): A solution of compound 23 (2.00 g, 12.1 mmol) in anhydrous THF (30 mL) was stirred in an ice bath under $N_2$ for 30 mins. Borane tetrahydrofuran complex solution (1 M, 30 mL) was added to the solution above dropwise over 30 mins using a syringe pump, while the temperature of the solution was maintained below 5° C. The resulting reaction mixture was left to stir in the ice bath and slowly warm to rt. After 24 h, the solution was placed in an ice bath again and excess borane reagent was destroyed by carefully adding MeOH until no gas evolved. The solvent was evaporated under reduced pressure and the residue was purified by flash column chromatography with silica gel, using DCM/Hexane as eluent, providing compound 24 (1.47 g, 80%) as an oil.

N-ethyl-3-methoxy-N-methylaniline (25): To a suspension of compound 24 (1.00 g, 6.61 mmol) and $Na_2CO_3$ (1.05 g, 9.92 mmol) in anhydrous MeCN (10 mL) under $N_2$ was added MeI (424 μL, 6.75 mmol) at rt. The reaction mixture was heated to 80° C. and stirred overnight. It was then cooled to room temperature, diluted with DCM, and filtered through Celite. The solvent was removed in vacuo, and the residue was purified by silica gel flash chromatography with silica gel (25 g), using DCM/Hexane as eluent to give compound 25 (917 mg, 84%) as a light yellow solid.

(E)-N-ethyl-3-methoxy-N-methyl-4-((4-nitrophenyl)diazenyl)aniline (26): Compound 25 (400 mg, 2.42 mmol) was dissolved in MeOH (1 mL). The solution was chilled in an ice bath, then treated with HCl (2 M, 10 mL). After 15 mins, p-nitrobenzenediazonium tetrafluoroborate (602 mg, 2.54 mmol) was added to the solution in 3 portions over an additional 15 mins, then stirred at 0° C. for 1 h. During this time, the color of the reaction mixture changed from orange to dark red. After two hours, the solution was carefully neutralized with solid $K_2CO_3$ until the pH value of the solution had risen above 7. The precipitate was collected via vacuum filtration and washed with small portions of DI water. The product was left in the funnel, air dried overnight, afforded compound 26 (714 mg, 94%) as a dark red solid, and used for the next step without further purification.

N-ethyl-N-(7-(ethyl(methyl)amino)-3H-phenoxazin-3-ylidene)ethanaminium (LGW14-49): Compounds 10 (30 mg, 0.182 mmol) and 26 (57 mg, 0.182 mmol) were dissolved in a solution of trifluoroethanol (3 mL) containing Trimethylsilyl polyphosphate (30 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{19}H_{24}N_3O$ [M]+310.1914; found 310.1943.

Scheme: Synthetic route to LGW 14-50.

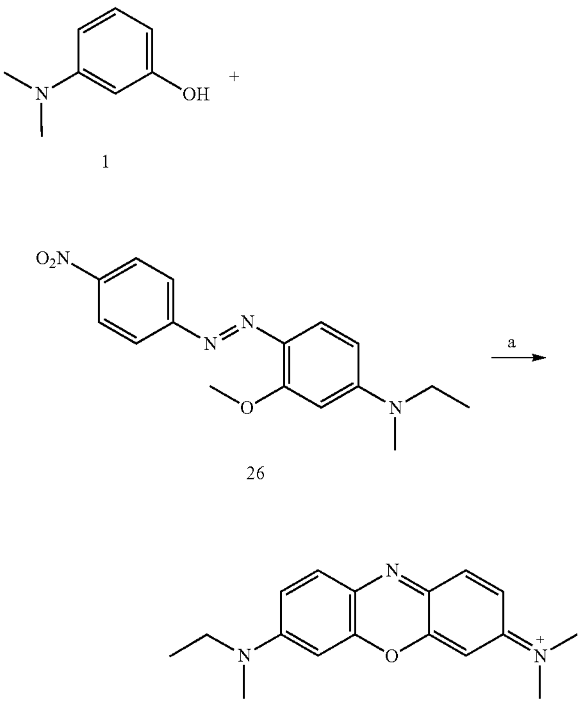

1

26

LGW14-50

Reagents and conditions: a) PPSE, $CF_3CH_2OH$, 80° C.

N-(7-(ethyl(methyl)amino)-3H-phenoxazin-3-ylidene)-N-methylmethanaminium (LGW14-50): Compounds 1 (30 mg, 0.219 mmol) and 26 (69 mg, 0.219 mmol) were dissolved in a solution of trifluoroethanol (3 mL) containing Trimethylsilyl polyphosphate (30 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{17}H_{20}N30$ [M]+282.1601; found 282.1626.

Scheme: Synthetic route to LGW 14-51.

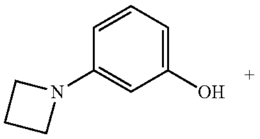

14

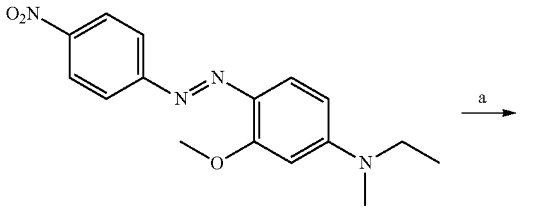

26

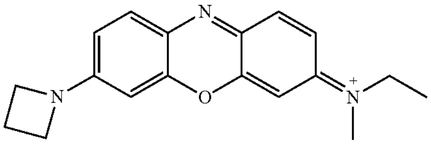

LGW14-51

Reagents and conditions: a) PPSE, $CF_3CH_2OH$, 80° C.

(E)-N-(7-(azetidin-1-yl)-3H-phenoxazin-3-ylidene)-N-methylethanaminium (LGW14-51): Compounds 14 (30 mg, 0.201 mmol) and 26 (63 mg, 0.201 mmol) were dissolved in a solution of trifluoroethanol (3 mL) containing Trimethylsilyl polyphosphate (30 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{18}H_{20}N30$ [M]+294.1601; found 294.1634.

Synthetic route to LGW 14-53.

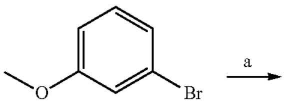

27

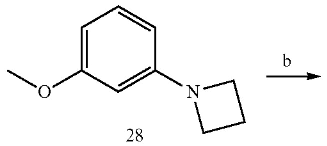

28

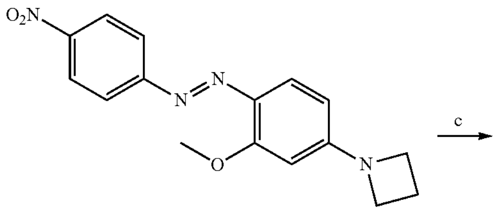

29

-continued

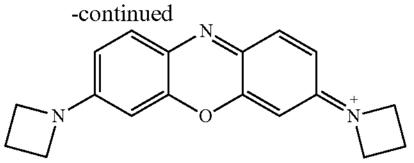

LGW14-53

Reagents and conditions: a) $Pd_2(dba)_3$, Xphos, $Cs_2CO_3$, azetidine, dioxane, 100° C.; b) i) 2M HCl, p-nitrobenzenediazonium tetrafluoroborate, 0° C.; ii) $K_2CO_3$, 0° C.; c) compound 14, PPSE, $CF_3CH_2OH$, 80° C.

1-(3-methoxyphenyl)azetidine (28): A flame-dried flask was charged with a magnetic stir bar, compound 27 (2.00 g, 10.7 mmol), $Pd_2(dba)_3$ (979 mg, 1.07 mmol), Xphos (1.53 g, 3.21 mmol), and $Cs_2CO_3$ (4.88 g, 14.97 mmol). The flask was sealed, evacuated under vacuum and backfilled 5 times with $N_2$ before the azetidine (800 μL, 11.8 mmol) and anhydrous dioxane (20 mL) was delivered via a syringe. The reaction was heated to 100° C. and stirred for 6 h, then cooled to rt, diluted with DCM (20 mL). The solid was removed via filtration through Celite, the filtrate was then deposited onto Celite, and concentrated to dryness. Purification by silica gel flash chromatography using a mobile phase of EtOAc and Hexanes provided compound 28 (1.58 g, 91%) as a yellow-orange solid.

(E)-1-(3-methoxy-4-((4-nitrophenyl)diazenyl)phenyl)azetidine (29): Compound 28 (400 mg, 2.45 mmol) was dissolved in MeOH (1 mL). The solution was chilled in an ice bath, then treated with HCl (2 M, 10 mL). After 15 mins, p-nitrobenzenediazonium tetrafluoroborate (639 mg, 2.70 mmol) was added to the solution in 3 portions over an additional 15 mins, then stirred at 0° C. for 1 h. During this time, the color of the reaction mixture changed from orange to dark red. After two hours, the solution was carefully neutralized with solid $K_2CO_3$ until the pH value of the solution had risen above 7. The precipitate was collected via vacuum filtration and washed with small portions of DI water. The product was left in the funnel, air dried overnight, afforded compound 29 (630 mg, 82%) as a black solid, and used for the next step without further purification.

1-(7-(azetidin-1-yl)-3H-phenoxazin-3-ylidene)azetidin-1-ium (LGW14-53): Compounds 14 (29 mg, 0.192 mmol) and 29 (60 mg, 0.192 mmol) were dissolved in a solution of trifluoroethanol (3 mL) containing Trimethylsilyl polyphosphate (30 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{18}H_{18}N_3O$ [M]+ 292.1444; found 292.1481.

Scheme: Synthetic route to LGW14-57.

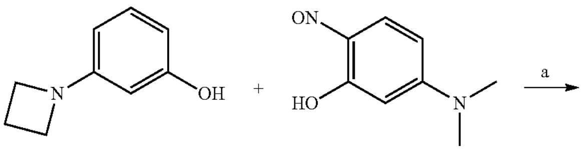

14 2

-continued

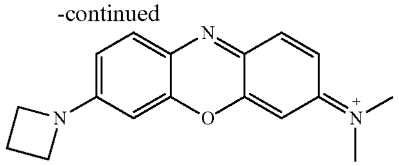

LGW14-57

Reagents and conditions: a) PPSE, $CF_3CH_2OH$, 80° C.

N-(7-(azetidin-1-yl)-3H-phenoxazin-3-ylidene)-N-methylmethanaminium (LGW14-57): Compounds 14 (30 mg, 0.201 mmol) and 2 (34 mg, 0.201 mmol) were dissolved in a solution of trifluoroethanol (3 mL) containing Trimethylsilyl polyphosphate (30 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{17}H_{18}N_3O$ [M]+280.1444; found 280.1491.

Scheme: Synthetic route to LGW14-61.

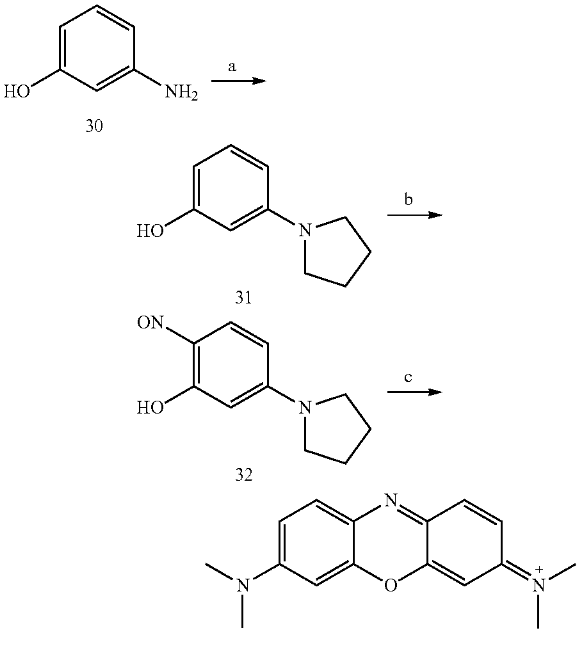

30

31

32

LGW14-61

Reagents and conditions: a) i) 1,4-dichlorobutane, toluene, reflux; ii) $Et_3N$, $Na_2CO_3$, reflux; b) 6M HCl, $NaNO_2$, 0° C.; c) compound 1, PPSE, $CF_3CH_2OH$, 80° C.

3-(pyrrolidin-1-yl)phenol (31): Following the protocol reported by Ghashang,[9] to a suspension of compound 30 (5.00 g, 45.82 mmol) in anhydrous toluene was added 1,4-dichlorobutane (5.52 mL, 50.4 mmol). The reaction mixture was refluxed for 24 h, then cooled to rt. Once cooled, $Et_3N$ (9.58 mL, 68.7 mmol) and $Na_2CO_3$ (4.86 g, 45.8 mmol) in 10 mL DI water was added to the reaction flask. The resulting reaction mixture was refluxed for an additional 24 h. Upon completion of the reaction, organic solvent was removed under reduced pressure, and the aqueous phase was extracted with DCM (3×100 mL). The combined organic layers were rinsed with brine, dried over anhydrous $Na_2SO_4$, and the solvent was removed using a rotary evaporator. The residue was purified by flash column chromatography with silica gel, using DCM/Hexane as eluent to give compound 31 (5.37 g, 72%) as a light gray solid.

2-nitroso-5-(pyrrolidin-1-yl)phenol (32): Compound 31 (400 mg, 2.45 mmol) was dissolved in an ice-cold 6 M HCl solution (4 mL). To the solution, $NaNO_2$ (178 mg, 2.57 mmol) was added portion wise over 1 h while maintaining the temperature of the solution below 5° C., such that no brown NOx vapors were observed. The reaction mixture was stirred for additional 2 h. After which, the precipitate was filtered through a Buchner funnel and washed with small portions of ice-cold 2 M HCl solution. The product was left in the funnel and air dried overnight to afford compound 32 (0.403 g, 86%) as a bright yellow solid, which was used for the next step without further purification.

1-(7-(dimethylamino)-3H-phenoxazin-3-ylidene)pyrrolidin-1-ium (LGW14-61): Compounds 1 (30 mg, 0.219 mmol) and 32 (42 mg, 0.219 mmol) were dissolved in a solution of trifluoroethanol (3 mL) containing Trimethylsilyl polyphosphate (30 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{18}H_{20}N30$ [M]+294.1601; found 294.1622.

Scheme: Synthetic route to LGW14-63.

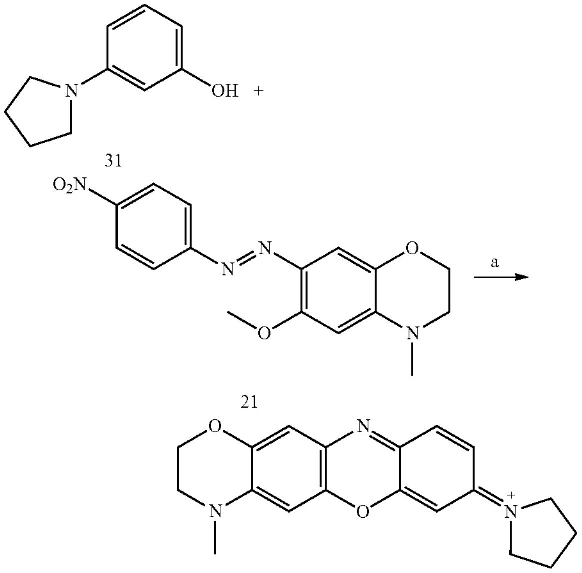

31

21

LGW14-63

Reagents and conditions: a) PPSE, $CF_3CH_2OH$, 80° C.

1-(4-methyl-3,4-dihydro-[1,4]oxazino[2,3-b]phenoxazin-8(2H)-ylidene)pyrrolidin-1-ium (LGW14-63): Compounds 31 (30 mg, 0.184 mmol) and 21 (61 mg, 0.184 mmol) were dissolved in a solution of trifluoroethanol (3 mL) containing Trimethylsilyl polyphosphate (30 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_1,H_{20}N_3O_2$ [M]+322.1550; found 322.1591.

Scheme: Synthetic route to LGW14-72.

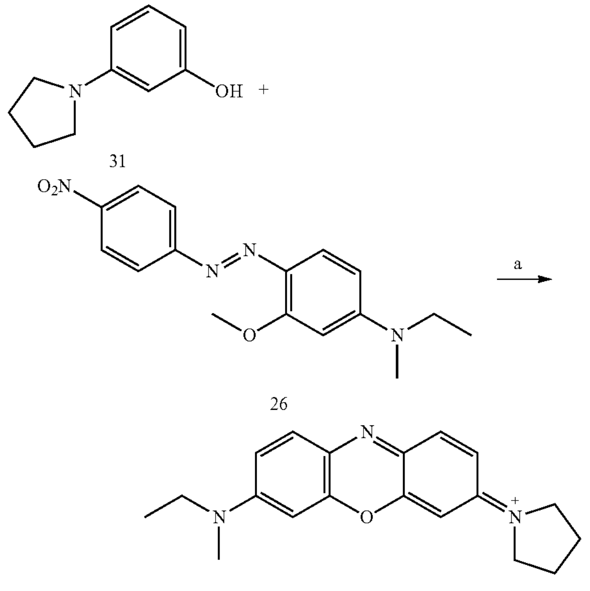

31

26

LGW14-72

Reagents and conditions: a) PPSE, $CF_3CH_2OH$, 80° C.

1-(7-(ethyl(methyl)amino)-3H-phenoxazin-3-ylidene)pyrrolidin-1-ium (LGW14-72): Compounds 31 (30 mg, 0.184 mmol) and 26 (58 mg, 0.184 mmol) were dissolved in a solution of trifluoroethanol (3 mL) containing Trimethylsilyl polyphosphate (30 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{19}H_{22}N_3O$ [M]+308.1757; found 308.1783.

Scheme: Synthetic route to LGW14-76.

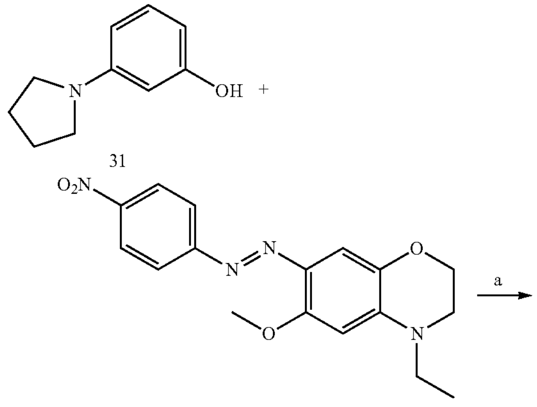

31

19

-continued

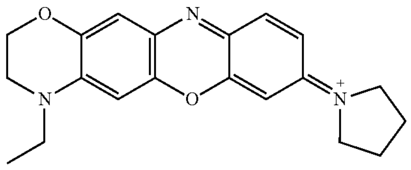

LGW14-76

Reagents and conditions: a) PPSE, $CF_3CH_2OH$, 80° C.

1-(4-ethyl-3,4-dihydro-[1,4]oxazino[2,3-b]phenoxazin-8(2H)-ylidene)pyrrolidin-1-ium (LGW14-76): Compounds 31 (30 mg, 0.184 mmol) and 19 (63 mg, 0.184 mmol) were dissolved in a solution of trifluoroethanol (3 mL) containing Trimethylsilyl polyphosphate (30 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{20}H_{22}N_3O_2$ [M]+336.1707; found 336.1753.

Scheme: Synthetic route to LGW14-76.

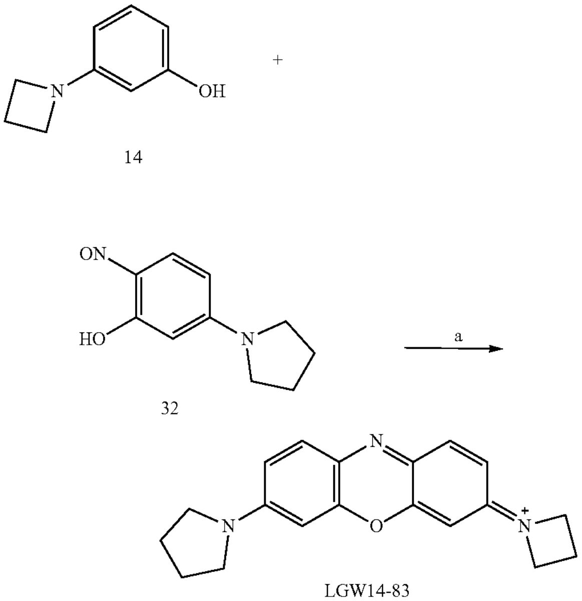

14

32

LGW14-83

Reagents and conditions: a) PPSE, $CF_3CH_2OH$, 80°C.

1-(7-(pyrrolidin-1-yl)-3H-phenoxazin-3-ylidene)azetidin-1-ium (LGW14-83): Compounds 14 (30 mg, 0.201 mmol) and 32 (39 mg, 0.201 mmol) were dissolved in a solution of trifluoroethanol (3 mL) containing Trimethylsilyl polyphosphate (30 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{19}H_{20}N30$ [M]+306.1601; found 306.1627.

Scheme: Synthetic route to LGW14-88.

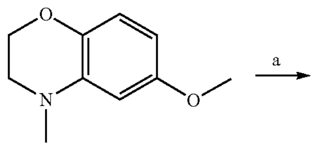

20

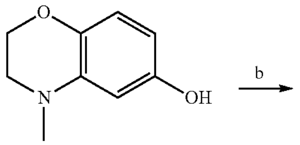

33

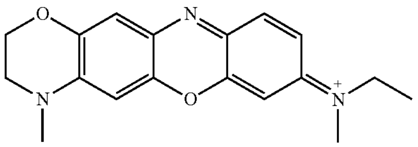

LGW14-88

Reagents and conditions: a) 1M $BBr_3$, DCM, 0° C. to rt; b) compound 26, PPSE, $CF_3CH_2OH$, 80° C.

4-methyl-3,4-dihydro-2H-benzo[b][1,4]oxazin-6-ol (33): Compound 20 (100 mg, 0.558 mmol) was dissolved in anhydrous DCM (5 mL) under $N_2$, and chilled in an ice bath. To the solution above, was added $BBr_3$ (1 M in DCM, 2 mL, 1.95 mmol) dropwise. The reaction mixture was slowly warmed up to rt and stirred overnight. The reaction flask was placed in an ice bath, after sufficient amount of time for cooling, water was carefully added to the reaction mixture to destroy excess $BBr_3$ and neutralized to pH ~7 with $Na_2CO_3$. The aqueous phase was then extracted with EtOAc (4×10 mL). The combined organics were dried over anhydrous $Na_2SO_4$, filtered, and concentrated in vacuo. Flash chromatography on silica gel yielded compound 33 (61 mg, 66%) as a burgundy oil.

(E)-N-methyl-N-(4-methyl-3,4-dihydro-[1,4]oxazino[2,3-b]phenoxazin-8(2H)-ylidene)ethanaminium (LGW14-88): Compounds 33 (10 mg, 0.061 mmol) and 26 (19 mg, 0.061 mmol) were dissolved in a solution of trifluoroethanol (1 mL) containing Trimethylsilyl polyphosphate (10 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{18}H_{20}N_3O_2$ [M]+ 310.1550; found 310.1578.

Scheme: Synthetic route to LGW14-90.

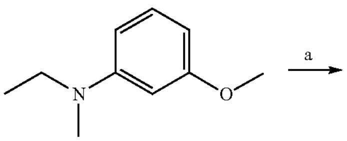

25

-continued

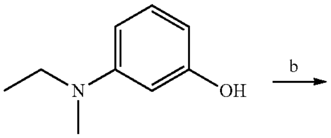

34

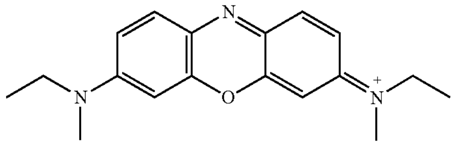

LGW14-90

Reagents and conditions: a) 1M $BBr_3$, DCM, 0° C. to rt; b) compound 26, PPSE, $CF_3CH_2OH$, 80° C.

3-(ethyl(methyl)amino)phenol (34): Compound 25 (100 mg, 0.605 mmol) was dissolved in anhydrous DCM (5 mL) under $N_2$, and chilled in an ice bath. To the solution above, was added $BBr_3$ (1 M in DCM, 2.2 mL, 2.12 mmol) dropwise. The reaction mixture was slowly warmed up to rt and stirred overnight. The reaction flask was placed in an ice bath, after sufficient amount of time for cooling, water was carefully added to the reaction mixture to destroy excess $BBr_3$ and neutralized to pH ~7 with $Na_2CO_3$. The aqueous phase was then extracted with EtOAc (4×10 mL). The combined organics were dried over anhydrous $Na_2SO_4$, filtered, and concentrated in vacuo. Flash chromatography on silica gel yielded compound 34 (75 mg, 82%) as a clear oil.

(E)-N-(7-(ethyl(methyl)amino)-3H-phenoxazin-3-ylidene)-N-methylethanaminium (LGW14-90): Compounds 34 (30 mg, 0.198 mmol) and 26 (62 mg, 0.198 mmol) were dissolved in a solution of trifluoroethanol (3 mL) containing Trimethylsilyl polyphosphate (30 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{18}H_{22}N_3O$ [M]+296.1757; found 296.1800.

Scheme: Synthetic route to LGW14-92.

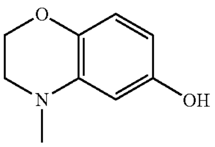

+

33

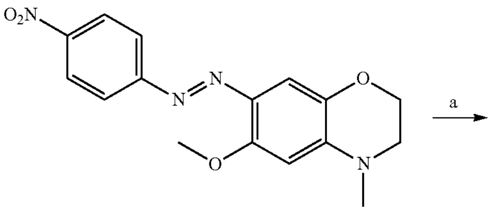

21

-continued

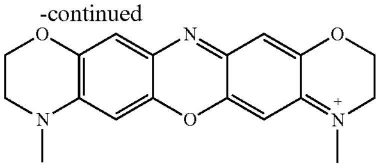

LGW14-92

Reagents and conditions: a) PPSE, $CF_3CH_2OH$, 80° C.

4,8-dimethyl-3,8,9,10-tetrahydro-2H-bis([1,4]oxazino)[2,3-b:3',2'-i]phenoxazin-4-ium (LGW14-92): Compounds 33 (10 mg, 0.061 mmol) and 21 (20 mg, 0.061 mmol) were dissolved in a solution of trifluoroethanol (1 mL) containing Trimethylsilyl polyphosphate (10 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{18}H_{18}N_3O_3$ [M]+324.1343, found 324.1361.

Scheme: Synthetic route to LGW14-95.

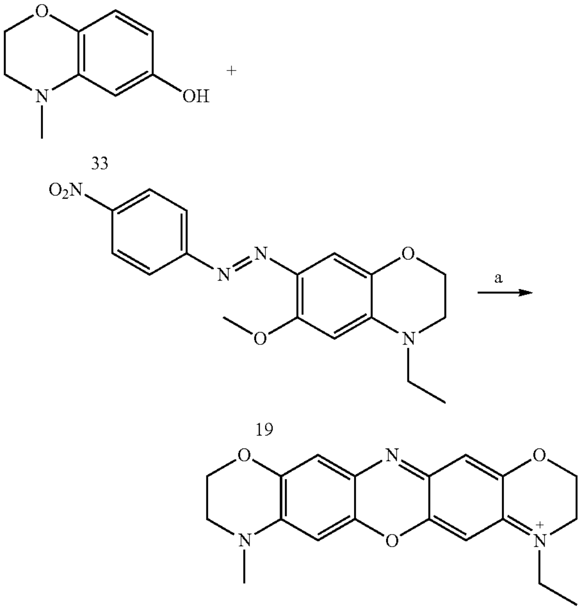

33

19

LGW14-95

Reagents and conditions: a) PPSE, $CF_3CH_2OH$, 80° C.

4-ethyl-8-methyl-3,8,9,10-tetrahydro-2H-bis([1,4]oxazino)[2,3-b:3',2'-i]phenoxazin-4-ium (LGW14-95): Compounds 33 (10 mg, 0.061 mmol) and 19 (21 mg, 0.061 mmol) were dissolved in a solution of trifluoroethanol (1 mL) containing Trimethylsilyl polyphosphate (10 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{19}H_{20}N_3O_3$ [M]+338.1499; found 338.1529.

Scheme: Synthetic route to LGW14-98.

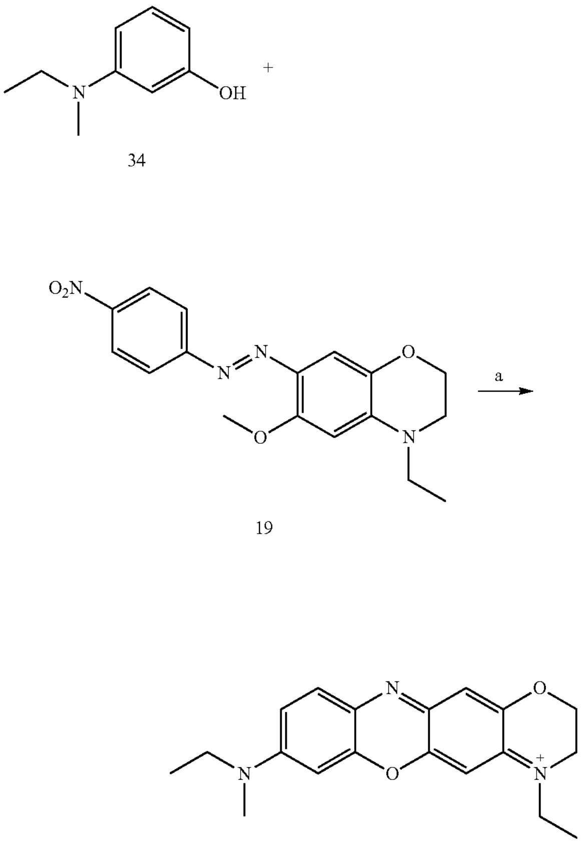

34

19

LGW14-98

Reagents and conditions: a) PPSE, $CF_3CH_2OH$, 80° C.

4-ethyl-8-(ethyl(methyl)amino)-2,3-dihydro-[1,4]oxazino[2,3-b]phenoxazin-4-ium (LGW14-98): Compounds 34 (30 mg, 0.198 mmol) and 19 (68 mg, 0.198 mmol) were dissolved in a solution of trifluoroethanol (3 mL) containing Trimethylsilyl polyphosphate (30 μL). The reaction mixture was heated to 80° C. and stirred overnight. It was then cooled to rt and the solvent was removed in vacuo. The residue was purified by silica gel flash chromatography using a mobile phase of $CHCl_3$ and MeOH containing 1% formic acid (gradient, 2-15% of MeOH in $CHCl_3$). MS(ESI): calcd for $C_{19}H_{22}N_3O_2$ [M]+324.1707; found 324.1722.

HPLC-MS characterization of oxazine derivative library. HPLC-MS was used to quantify the purity of each oxazine derivative via area under the curve (AUC) analysis of the absorbance at 254 nm (left) and mass to charge (m/z) ratio in positive ion mode (right). Sample (5 μL) was injected into a $C_{18}$ column (Poroshell 120, 2.1×50 mm, 2.7 micron), and eluted with a solvent system of A ($H_2O$, 0.1% formic acid) and B (Acetonitrile, 0.1% formic acid) at 0.4 mL/min, from A/B=95/5 to 5/95 over 6 min, maintained at A/B=5/95 for additional 2 min. Ions were detected in positive ion mode by setting the capillary voltage at 4 kV and gas temperature at 350° C. Purity of 97% was determined for LGW-76 and purity of >99% for LGW-13-79, LGW14-42, LGW14-47, LGW14-51, LGW14-53, and LGW14-83.

Tabulated spectral and physicochemical properties of screening candidates.

| Compound | Molecular weight (g/mol) | $\lambda_{abs}$ (nm) | ε ($M^{-1}$ $cm^{-1}$) | $FWHM_{abs}$ (nm) | $\lambda_{em}$ (nm) | Stokes Shift (nm) | $FWHM_{em}$ (nm) | Φ | Brightness ($M^{-1}cm^{-1}$) | Log $D_{7.4}$ |
|---|---|---|---|---|---|---|---|---|---|---|
| LGW13-79 | 308.40 | 648 | 54,700 | 72 | 669 | 21 | 41 | 0.08 | 4.27 | 0.8 |
| LGW14-42 | 322.39 | 654 | 56,000 | 76 | 679 | 25 | 46 | 0.14 | 7.62 | 0.5 |
| LGW14-47 | 308.36 | 651 | 46,700 | 78 | 677 | 26 | 47 | 0.14 | 6.35 | 0.1 |
| LGW14-51 | 294.38 | 644 | 42,000 | 76 | 665 | 21 | 42 | 0.10 | 4.28 | 0.5 |
| LGW14-53 | 292.36 | 644 | 70,400 | 73 | 666 | 22 | 41 | 0.22 | 15.77 | 0.3 |
| LGW14-83 | 306.39 | 647 | 50,000 | 76 | 669 | 22 | 43 | 0.20 | 10.00 | 0.5 |

FIGS. 1A through 1F represent normalized absorption and fluorescence emission spectra of oxazine derivatives in PBS. Compounds LGW14-42 and LGW14-27 are both absorbing and emitting in the NIR, while the rest only emit in the NIR. LGW14-42 is the most red-shifted fluorophore among the 7 screened candidate compounds.

Figure 2A:
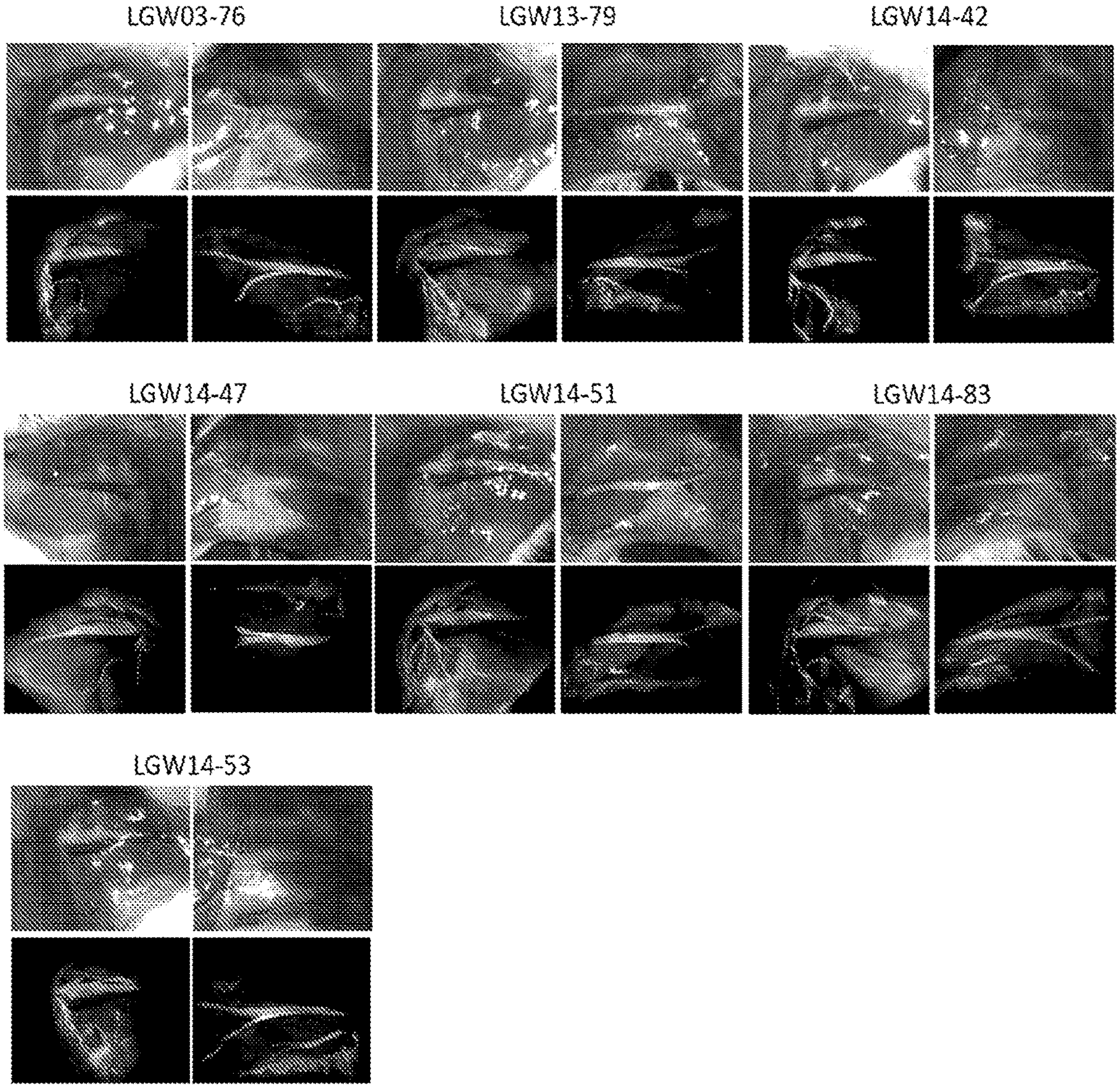
FIG. 2A provides representative photographs and fluorescence images of the NIR oxazine derivatives after direct application (125 μM in co-solvent formulation) of indicated compounds to exposed brachial plexus and sciatic nerves.
Figure 2B:
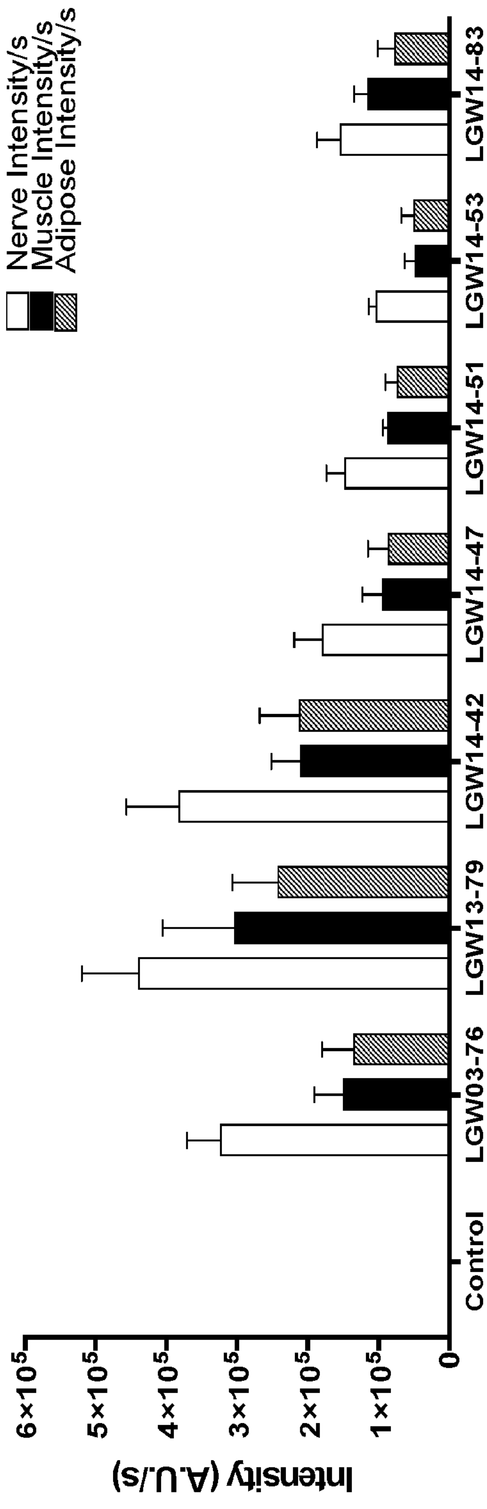
FIG. 2B represents the average nerve (white), muscle (black) and adipose (gray) tissue intensities per second were quantified in comparison to an unstained control group.
Figure 2C:
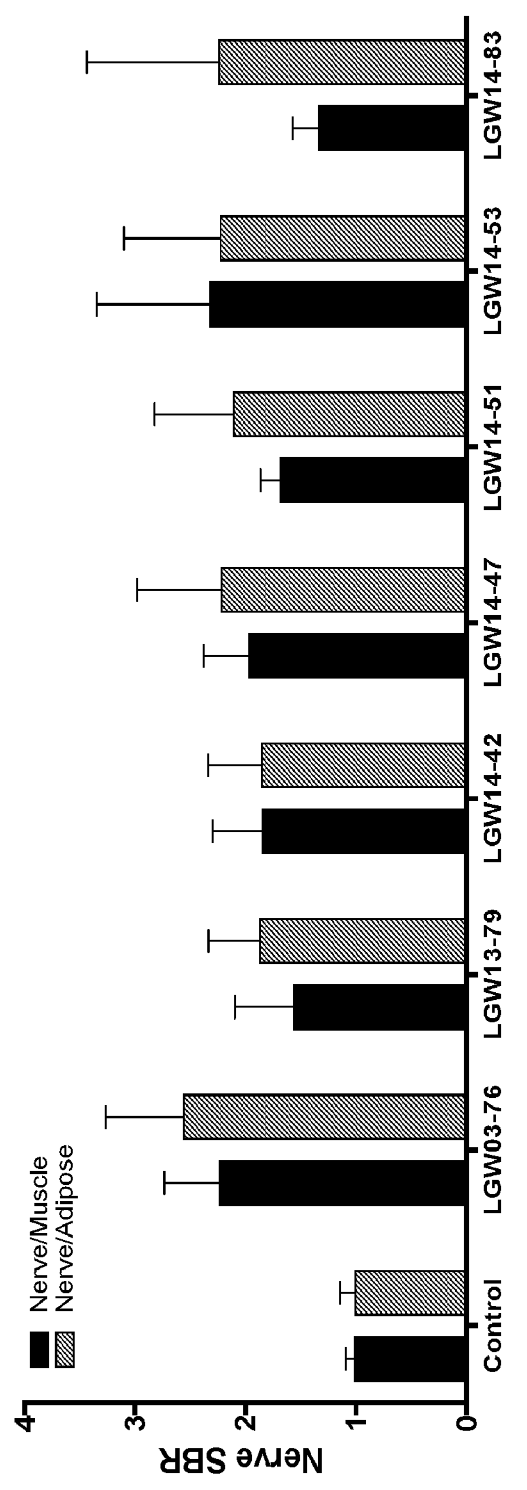
FIG. 2C represents quantified nerve signal to background ratios (SBRs) calculated for comparison between the screened oxazine derivatives and unstained control group.

FIGS. 2A-2C—In vivo direct administration nerve-specificity screening. FIG. 2A. Representative photographs, and fluorescence images of the NIR oxazine derivatives after direct application (125 μM in co-solvent formulation) to exposed brachial plexus and sciatic nerves. All images are representative of data collected for n=6 nerve sites per fluorophore. FIG. 2B. The average nerve (white), muscle (black) and adipose (gray) tissue intensities per second were quantified in comparison to an unstained control group. FIG. 2C. Quantified nerve SBRs were calculated for comparison between the screened oxazine derivatives and unstained control group.

Figure 3A:
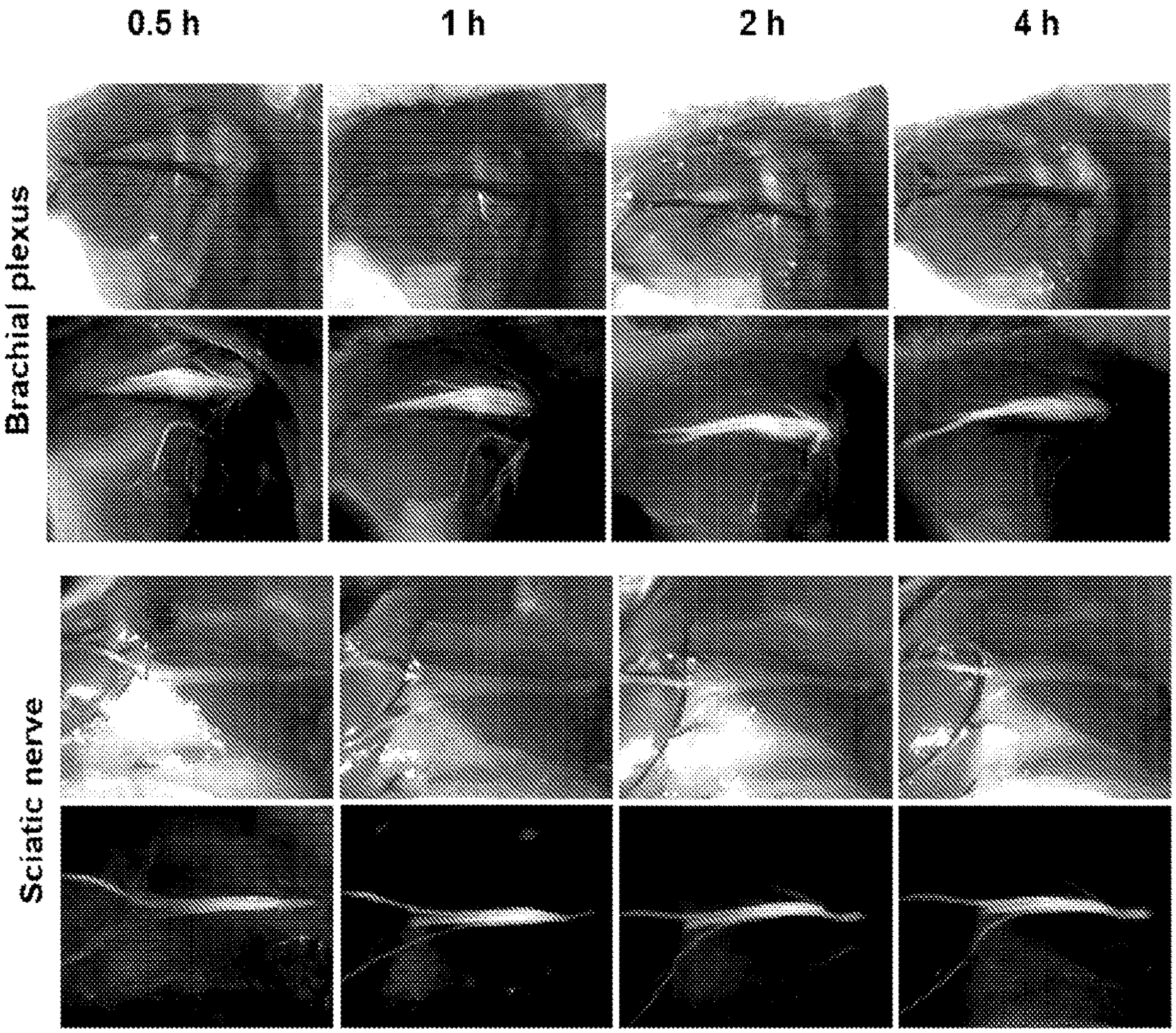
FIG. 3A provides photographs and fluorescence images of the NIR nerve-specific candidate LGW03-76 after systemic administration at 0.5, 1, 2, and 4 h time points.
Figure 3B:
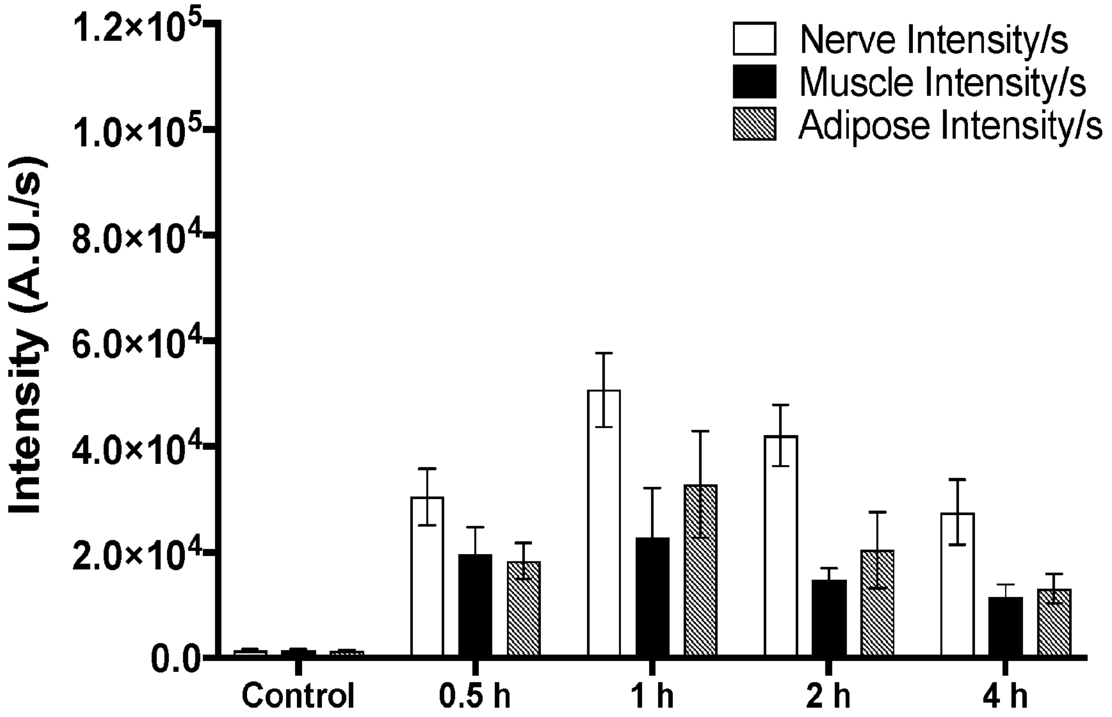
FIG. 3B represents average nerve (white), muscle (black) and adipose (gray) tissue intensities per second that were quantified and compared to a control tissue autofluorescence.
Figure 3C:
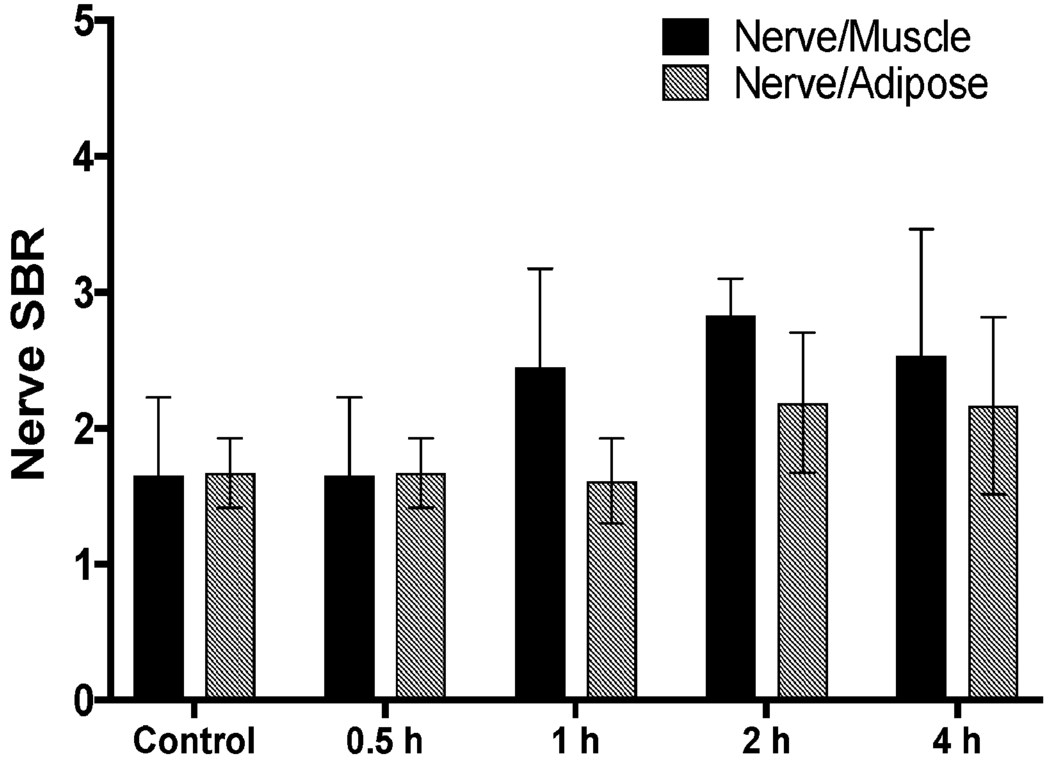
FIG. 3C represents quantified nerve SBRs calculated for comparison between LGW03-76 and control tissue autofluorescence.

All quantified data is presented as the mean±standard deviation. FIGS. 3A-3C—Pharmacokinetic studies of NIR nerve-specific candidate LGW03-76. FIG. 3A. Representative photographs and fluorescence images of the NIR nerve-specific candidate LGW03-76 after systemic administration at 0.5, 1, 2, and 4 h time points. FIG. 3B. The average nerve (white), muscle (black) and adipose (gray) tissue intensities per second were quantified and compared to a control tissue autofluorescence. FIG. 3C. Quantified nerve SBRs were calculated for comparison between LGW03-76 and control tissue autofluorescence. All quantified data is presented as the mean±standard deviation.

Figure 4A:
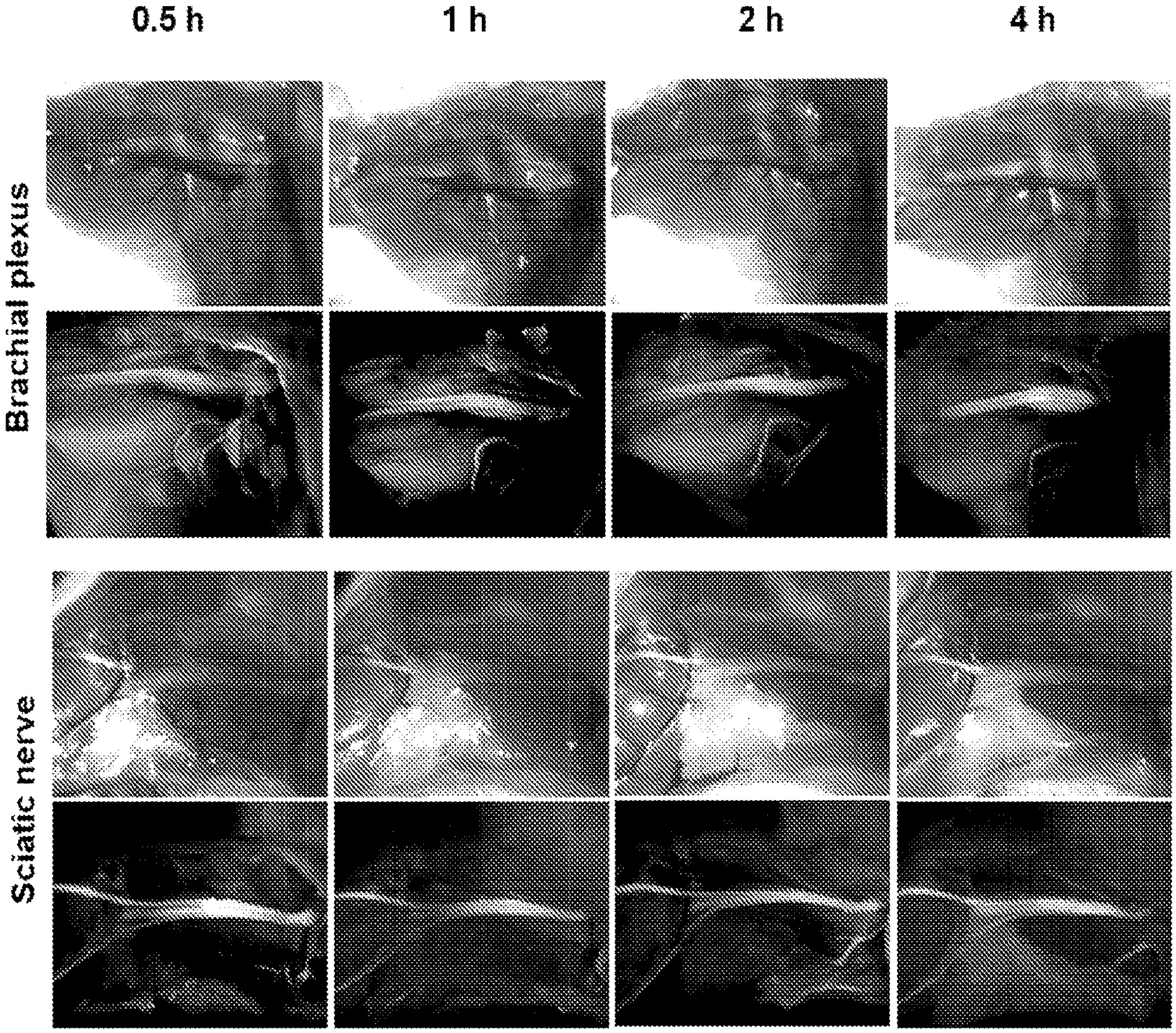
FIG. 4A provides photographs and fluorescence images of the NIR nerve-specific candidate LGW13-79 after systemic administration at 0.5, 1, 2, and 4 h time points.
Figure 4B:
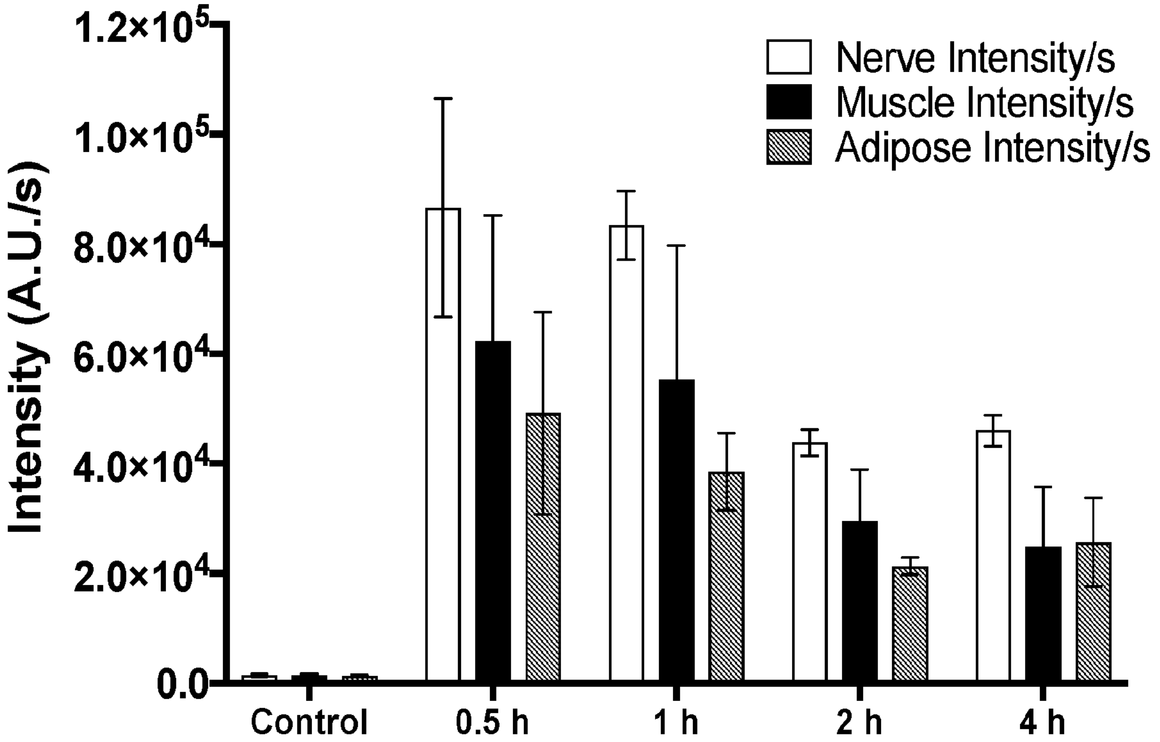
FIG. 4B represents average nerve (white), muscle (black) and adipose (gray) tissue intensities per second that were quantified and compared to a control tissue autofluorescence.
Figure 4C:
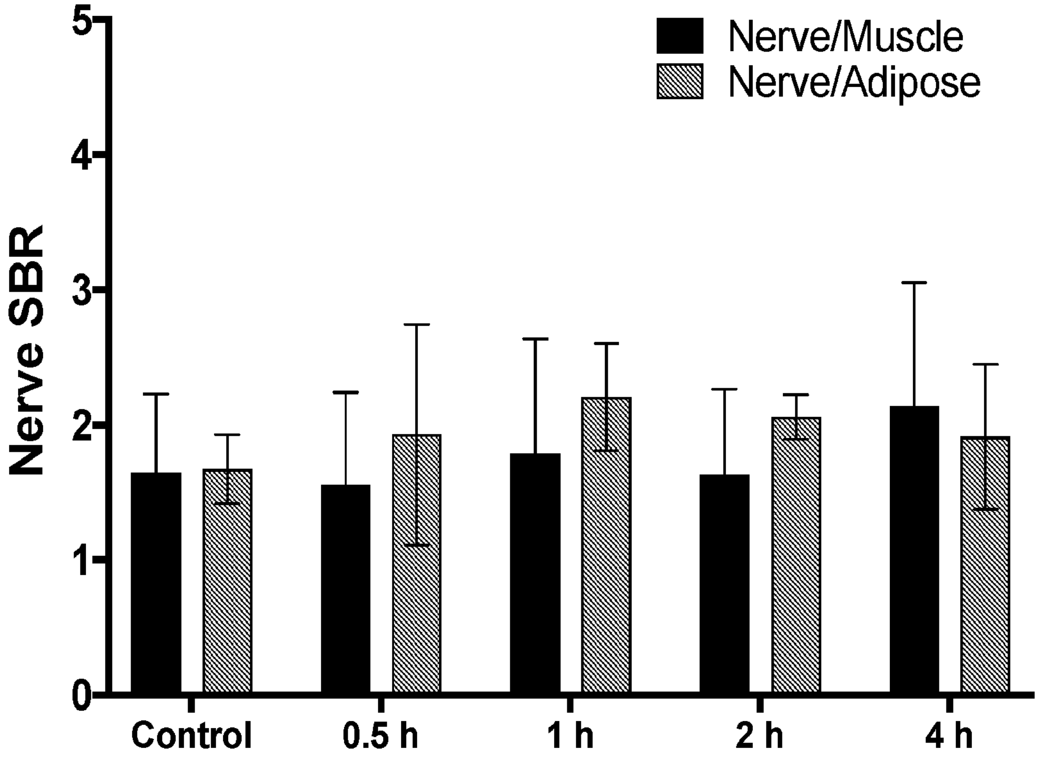
FIG. 4C represents quantified nerve SBRs calculated for comparison between LGW13-79 and control tissue autofluorescence.

FIGS. 4A-4C—Pharmacokinetic studies of NIR nerve-specific candidate LGW13-79. FIG. 4A. Representative photographs and fluorescence images of the NIR nerve-specific candidate LGW13-79 after systemic administration at 0.5, 1, 2, and 4 h time points. FIG. 4B. The average nerve (white), muscle (black) and adipose (gray) tissue intensities per second were quantified and compared to a control tissue autofluorescence. FIG. 4C. Quantified nerve SBRs were calculated for comparison between LGW13-79 and control tissue autofluorescence. All quantified data is presented as the mean±standard deviation.

Figure 5A:
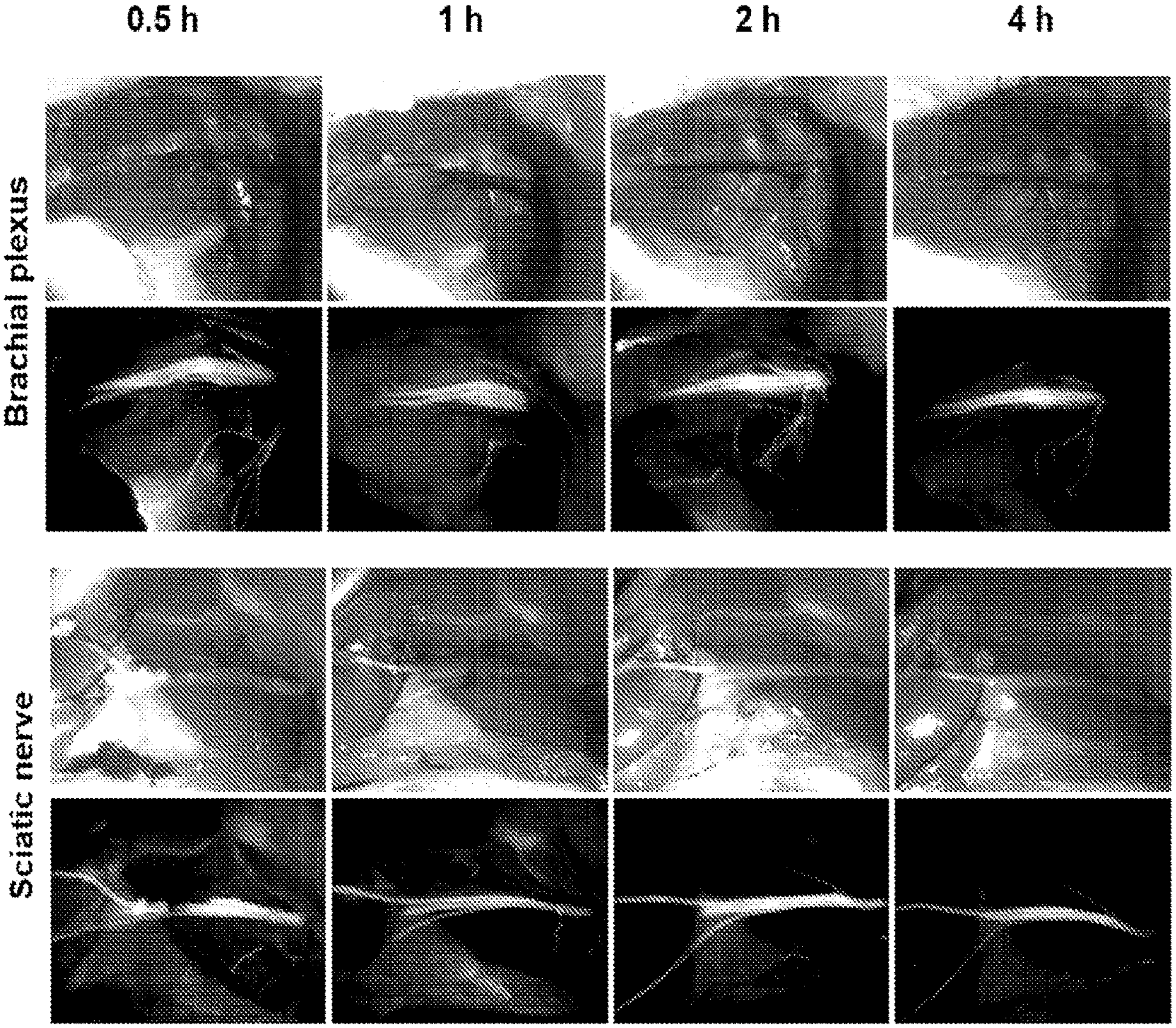
FIG. 5A provides representative photographs and fluorescence images of the NIR nerve-specific candidate LGW14-42 after systemic administration at 0.5, 1, 2, and 4 h time points.
Figure 5B:
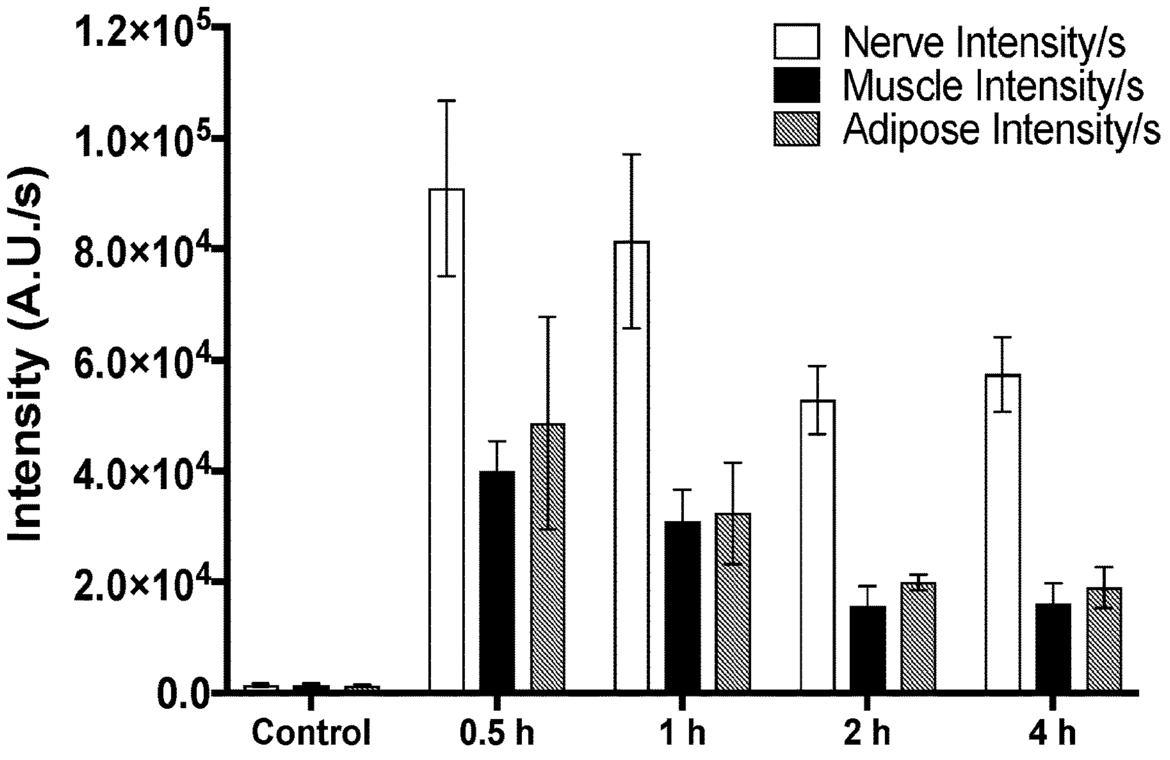
FIG. 5B represents average nerve (white), muscle (black) and adipose (gray) tissue intensities per second that were quantified and compared to a control tissue autofluorescence.
Figure 5C:
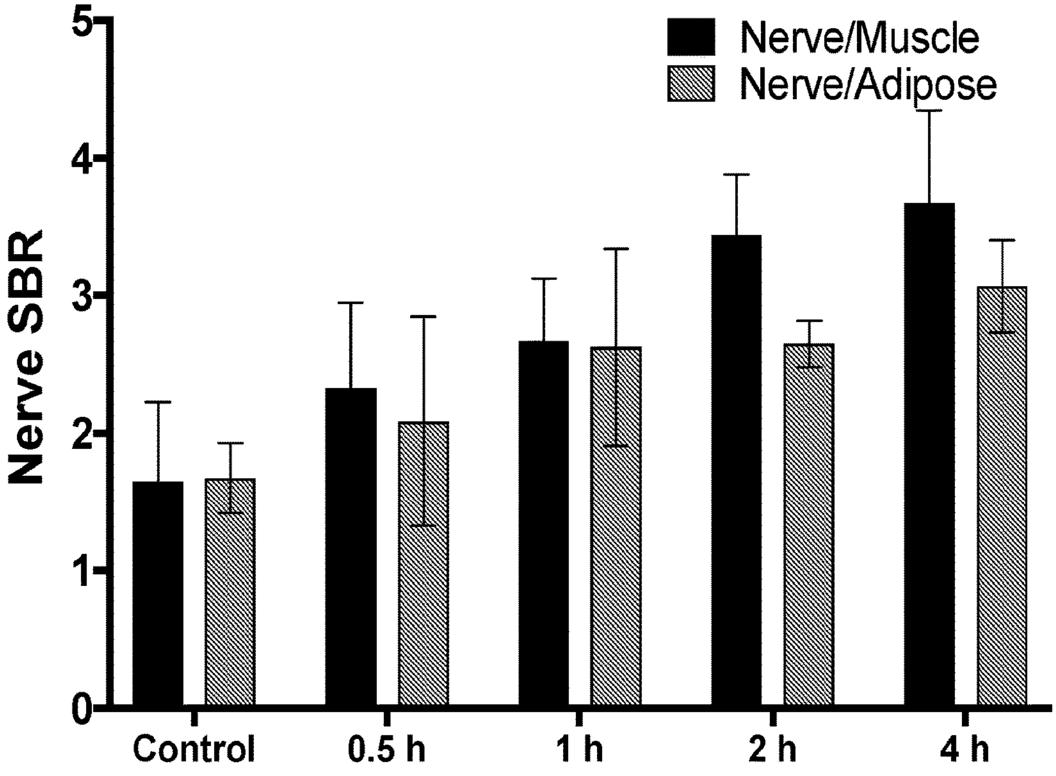
FIG. 5C represents quantified nerve SBRs calculated for comparison between LGW14-42 and control tissue autofluorescence.

FIGS. 5A-5C—Pharmacokinetic studies of NIR nerve-specific candidate LGW14-42. FIG. 5A. Representative photographs and fluorescence images of the NIR nerve-specific candidate LGW14-42 after systemic administration at 0.5, 1, 2, and 4 h time points. FIG. 5B. The average nerve (white), muscle (black) and adipose (gray) tissue intensities per second were quantified and compared to a control tissue autofluorescence. FIG. 5C. Quantified nerve SBRs were calculated for comparison between LGW14-42 and control tissue autofluorescence. All quantified data is presented as the mean±standard deviation.

Experimental LogD measurements. Each screening candidate was dissolved in DMSO at a concentration of 10 mM. The stock solution was sampled (2 μL) and added to a 1 mL mixture of 1-octanol and PBS buffer (equal volume). The solution was then vortexed for 30 mins at room temperature before centrifuged at 13,000 rpm for 5 minutes. The PBS buffer and 1-octanol layers were separated and measured for absorbance using a SpectraMax M5 spectrometer with a Microplate reader (Molecular Devices, Sunnyvale, CA). Sample concentration in each phase was then calculated using Beer's Law plots of absorbance versus concentration. The experimental LogD value for each screening candidates was calculated using the equation below.

$$\text{Log}D = \text{Log}\left(\frac{\text{Sample concentration in } PBS \text{ buffer}}{\text{Sample } concetration \text{ in } 1-\text{octanol}}\right)$$

REFERENCES

1. Chance, B. Near-infrared images using continuous, phase-modulated, and pulsed light with quantitation of blood and blood oxygenation. *Annals of the New York Academy of Sciences* 838, 29-45 (1998).
2. Vahrmeijer, A. L., Hutteman, M., van der Vorst, J. R., van de Velde, C. J. & Frangioni, J. V. Image-guided cancer surgery using near-infrared fluorescence. *Nature reviews. Clinical oncology* 10, 507-518 (2013).
3. Frangioni, J. V. In vivo near-infrared fluorescence imaging. *Current opinion in chemical biology* 7, 626-634 (2003).
4. Gibbs, S. L. Near infrared fluorescence for image-guided surgery. *Quantitative imaging in medicine and surgery* 2, 177-187 (2012).
5. Whitney, M. A. et al. Fluorescent peptides highlight peripheral nerves during surgery in mice. *Nature biotechnology* 29, 352-356 (2011).
6. Wu, C. et al. Molecular probes for imaging myelinated white matter in CNS. *Journal of medicinal chemistry* 51, 6682-6688 (2008).
7. Wang, C. et al. In situ fluorescence imaging of myelination. *The journal of histochemistry and cytochemistry: official journal of the Histochemistry Society* 58, 611-621 (2010).
8. Stankoff, B. et al. Imaging of CNS myelin by positron-emission tomography. *Proceedings of the National Academy of Sciences of the United States of America* 103, 9304-9309 (2006).
9. Cotero, V. E. et al. Intraoperative fluorescence imaging of peripheral and central nerves through a myelin-selective contrast agent. *Molecular imaging and biology: MIB: the official publication of the Academy of Molecular Imaging* 14, 708-717 (2012).

10. Gibbs, S. L. et al. Structure-activity relationship of nerve-highlighting fluorophores. *PLoS One* 8, e73493 (2013).

11. Gibbs-Strauss, S. L. et al. Nerve-highlighting fluorescent contrast agents for image-guided surgery. *Molecular imaging* 10, 91-101 (2011).

12. Meyers, J. R. et al. Lighting up the senses: FM1-43 loading of sensory cells through nonselective ion channels. *The Journal of neuroscience: the official journal of the Society for Neuroscience* 23, 4054-4065 (2003).

13. Gibbs-Strauss, S. L. et al. Molecular imaging agents specific for the annulus fibrosus of the intervertebral disk. *Molecular imaging* 9, 128-140 (2010).

14. Park, M. H. et al. Prototype nerve-specific near-infrared fluorophores. *Theranostics* 4, 823-833 (2014).

15. Wang, C. et al. Longitudinal near-infrared imaging of myelination. *The Journal of neuroscience: the official journal of the Society for Neuroscience* 31, 2382-2390 (2011).

16. Barth, C. W. & Gibbs, S. L. Direct Administration of Nerve-Specific Contrast to Improve Nerve Sparing Radical Prostatectomy. *Theranostics* 7, 573-593 (2017).

17. Ghashang, M. ZnAl2O4-Bi2O3 composite nano-powder as an efficient catalyst for the multi-component, one-pot, aqueous media preparation of novel 4H-chromene-3-carbonitriles. *Research on Chemical Intermediates* 42, 4191-4205 (2016).

18. Grimm, J. B. et al. A general method to improve fluorophores for live-cell and single-molecule microscopy. *Nat Methods* 12, 244-250, 243 p following 250 (2015).

19. Zhang, H. et al. Design, synthesis and characterization of potent microtubule inhibitors with dual anti-proliferative and anti-angiogenic activities. *European Journal of Medicinal Chemistry* 157, 380-396 (2018).

What is claimed:

1. A compound of Formula (II):

(II)

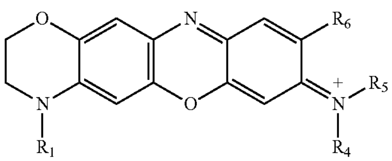

wherein:

$R_1$ is selected from the group consisting of a straight or branched $C_1$-$C_6$ alkyl; $-(CH_2)_{n1}-SO_3^-$; $-(CH_2)_{n1}-N^+(CH_3)_3$; $-CH_2-CH_2-O-X_1$; $-CH_2-CH_2-O-[CH_2-CH_2-O]_{n2}-X_1$; $-CH_2-CH_2-CH_2-O-X_1$; and $-CH_2-CH_2-CH_2-O-[CH_2-CH_2-CH_2-O]_{n3}-X_1$; or a moiety selected from the group consisting of:

a)

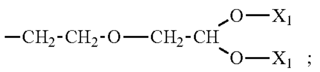

b)

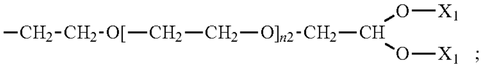

-continued c)

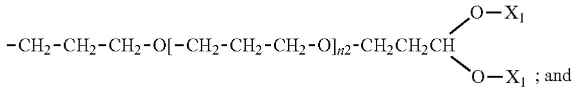

d)

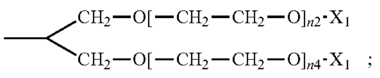

$R_4$ and $R_5$, together with the nitrogen atom to which they are bound, form a ring selected from the group consisting of:

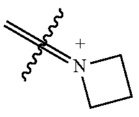 and 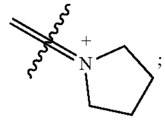;

$R_6$ is hydrogen;

$X_1$ in each instance is independently selected from the group consisting of $C_1$-$C_6$ straight or branched alkyl, $C_1$-$C_6$ straight or branched alkenyl, $C_1$-$C_6$ straight or branched alkynyl, and $-Si(C_1$-$C_4$ alkyl$)_3$;

n is an integer selected from the group of 1 and 2;

n1 is an integer independently selected in each instance from the group consisting of 1, 2, 3, and 4;

n2 is an integer independently selected in each instance from the group consisting of 1, 2, 3, 4, 5, 6, 7, 8, 9, and 10;

n3 is an integer independently selected in each instance from the group consisting of 1, 2, 3, 4, 5, 6, 7, 8, 9, and 10;

n4 is an integer independently selected in each instance from the group consisting of 1, 2, 3, 4, 5, 6, 7, 8, 9, and 10; and with the proviso that the sum of n2+n2 is not greater than 10;

with the proviso that the sum of n2+n3 is not greater than 10;

with the proviso that the sum of n2+n4 is not greater than 10; and with the proviso that the sum of n3+n4 is not greater than 10.

2. The compound of claim 1, the compound having Formula (V):

(V)

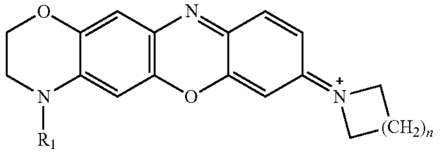

wherein:

$R_1$ is selected from the group consisting of a straight or branched $C_1$-$C_6$ alkyl; $-(CH_2)_{n1}-SO_3^-$; $-(CH_2)_{n1}-N^+(CH_3)_3$; $-CH_2-CH_2-O-X_1$; $-CH_2-CH_2-O-[CH_2-CH_2-O]_{n2}-X_1$; $-CH_2-CH_2-CH_2-O-X_1$; and $-CH_2-CH_2-CH_2-O-[CH_2-CH_2-CH_2-O]_{n3}-X_1$; or a moiety selected from the group consisting of:

a)

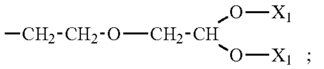

b)

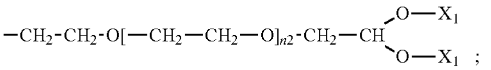

c)

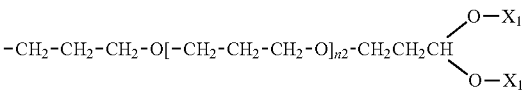

; and d)

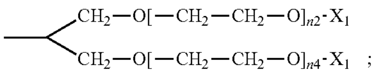

$X_1$ in each instance is independently selected from the group consisting of $C_1$-$C_6$ straight or branched alkyl, $C_1$-$C_6$ straight or branched alkenyl, $C_1$-$C_6$ straight or branched alkynyl, and —Si($C_1$-$C_4$ alkyl)$_3$;

n is an integer selected from the group consisting of 1 and 2;

n1 is an integer independently selected in each instance from the group consisting of 1, 2, 3, and 4;

n2 is an integer independently selected in each instance from the group consisting of 1, 2, 3, 4, 5, 6, 7, 8, 9, and 10;

n3 is an integer independently selected in each instance from the group consisting of 1, 2, 3, 4, 5, 6, 7, 8, 9, and 10;

n4 is an integer independently selected in each instance from the group consisting of 1, 2, 3, 4, 5, 6, 7, 8, 9, and 10; and with the proviso that the sum of n2+n2 is not greater than 10;

with the proviso that the sum of n2+n3 is not greater than 10;

with the proviso that the sum of n2+n4 is not greater than 10; and with the proviso that the sum of n3+n4 is not greater than 10.

3. The compound of claim 1, the compound having Formula (Va):

(Va)

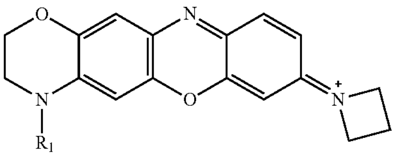

wherein:

$R_1$ is selected from the group consisting of a straight or branched $C_1$-$C_6$ alkyl; —$(CH_2)_{n1}$—$SO_3^-$; —$(CH_2)_{n1}$—$N^+(CH_3)_3$; —$CH_2$—$CH_2$—O—$X_1$; —$CH_2$—$CH_2$—O—[$CH_2$—$CH_2$—O]$_{n2}$—$X_1$; —$CH_2$—$CH_2$—$CH_2$—O—$X_1$; and —$CH_2$—$CH_2$—$CH_2$—O—[$CH_2$—$CH_2$—$CH_2$—O]$_{n3}$—$X_1$; or a moiety selected from the group consisting of:

a)

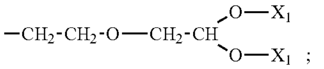

b)

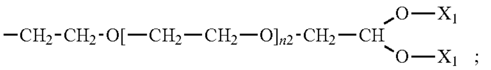

c)

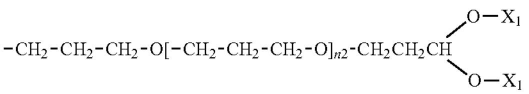

; and d)

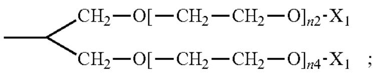

$X_1$ in each instance is independently selected from the group consisting of C1-C6 straight or branched alkyl, $C_1$-$C_6$ straight or branched alkenyl, $C_1$-$C_6$ straight or branched alkynyl, and —Si($C_1$-$C_4$ alkyl)$_3$;

n is an integer selected from the group consisting of 1 and 2;

n1 is an integer independently selected in each instance from the group consisting of 1, 2, 3, and 4;

n2 is an integer independently selected in each instance from the group consisting of 1, 2, 3, 4, 5, 6, 7, 8, 9, and 10;

n3 is an integer independently selected in each instance from the group consisting of 1, 2, 3, 4, 5, 6, 7, 8, 9, and 10;

n4 is an integer independently selected in each instance from the group consisting of 1, 2, 3, 4, 5, 6, 7, 8, 9, and 10; and with the proviso that the sum of n2+n2 is not greater than 10;

with the proviso that the sum of n2+n3 is not greater than 10;

with the proviso that the sum of n2+n4 is not greater than 10; and with the proviso that the sum of n3+n4 is not greater than 10.

4. The compound of claim 1, the compound having the formula (II):

(II)

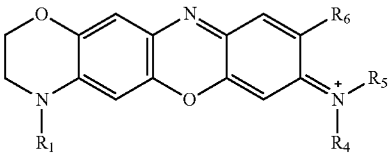

wherein:

$R_1$ is selected from the group consisting of a straight or branched $C_1$-$C_6$ alkyl; —$(CH_2)_{n1}$—$SO_3^-$; —$(CH_2)_{n1}$—$N^+(CH_3)_3$; —$CH_2$—$CH_2$—O—$X_1$; —$CH_2$—$CH_2$—O—[$CH_2$—$CH_2$—O]$_{n2}$—$X_1$; —$CH_2$—$CH_2$—$CH_2$—O—$X_1$; and —$CH_2$—$CH_2$—$CH_2$—O—[$CH_2$—$CH_2$—$CH_2$—O]$_{n3}$—$X_1$; or a moiety selected from the group consisting of:

a)

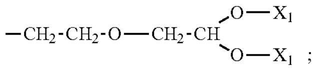

b)

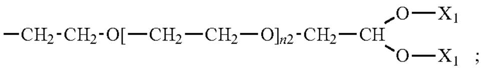

c)

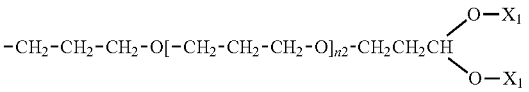

; and

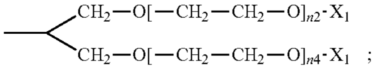

$X_1$ in each instance is independently selected from the group consisting of $C_1$-$C_6$ straight or branched alkyl, $C_1$-$C_6$ straight or branched alkenyl, $C_1$-$C_6$ straight or branched alkynyl, and —$Si(C_1$-$C_4$ alkyl$)_3$;

n1 is an integer independently selected in each instance from the group consisting of 1, 2, 3, and 4;

n2 is an integer independently selected in each instance from the group consisting of 1, 2, 3, 4, 5, 6, 7, 8, 9, and 10;

n3 is an integer independently selected in each instance from the group consisting of 1, 2, 3, 4, 5, 6, 7, 8, 9, and 10; and n4 is an integer independently selected in each instance from the group consisting of 1, 2, 3, 4, 5, 6, 7, 8, 9, and 10;

$R_4$ and $R_5$, together with the nitrogen atom to which they are bound, form a ring selected from the group consisting of:

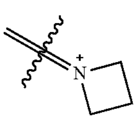 and 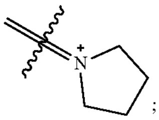 ;

$R_6$ is hydrogen;

with the proviso that the sum of n2+n4 is not greater than 10; and with the proviso that, when $R_1$ is methyl and $R_4$ is ethyl, $R_5$ is not ethyl.

5. The compound of claim 4, wherein $R_1$ is selected from the group consisting of straight or branched $C_1$-$C_3$ alkyl.

6. The compound of claim 1, the compound having the Formula (V):

(V)

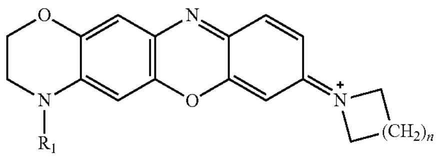

wherein:

$R_1$ is selected from the group consisting of a straight or branched $C_1$-$C_6$ alkyl; $-(CH_2)_{n1}-SO_3^-$; $-(CH_2)_{n1}-N^+(CH_3)_3$; $-CH_2-CH_2-O-X_1$; $-CH_2-CH_2-O-[CH_2-CH_2-O]_{n2}-X_1$; $-CH_2-CH_2-CH_2-O-X_1$; and $-CH_2-CH_2-CH_2-O-[CH_2-CH_2-CH_2-O]_{n3}-X_1$; or a moiety selected from the group consisting of:

a)

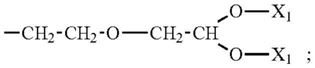

b)

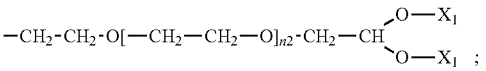

c)

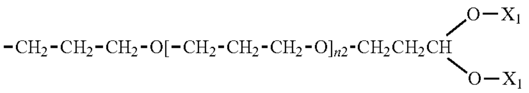

; and d)

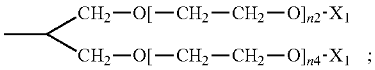

$X_1$ in each instance is independently selected from the group consisting of $C_1$-$C_6$ straight or branched alkyl, $C_1$-$C_6$ straight or branched alkenyl, $C_1$-$C_6$ straight or branched alkynyl, and- —$Si(C_1$-$C_4$ alkyl$)_3$;

n is an integer selected from the group consisting of 1 and 2;

n1 is an integer independently selected in each instance from the group consisting of 1, 2, 3, and 4;

n2 is an integer independently selected in each instance from the group consisting of 1, 2, 3, 4, 5, 6, 7, 8, 9, and 10;

n3 is an integer independently selected in each instance from the group consisting of 1, 2, 3, 4, 5, 6, 7, 8, 9, and 10; and n4 is an integer independently selected in each instance from the group consisting of 1, 2, 3, 4, 5, 6, 7, 8, 9, and 10;

with the proviso that the sum of n2+n4 is not greater than 10.

7. The compound of claim 6, wherein the compound has the formula:

(VIIIa)

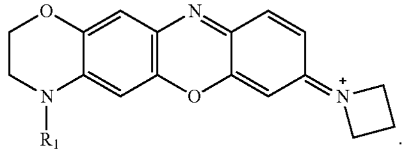

8. The compound of claim 6, wherein the compound has the formula:

(VIIIb)

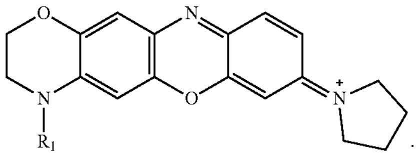

9. A compound of claim 1 selected from the group consisting of:

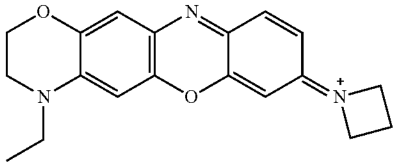

,

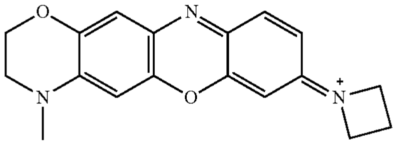

,

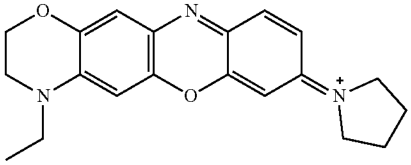

, and

-continued

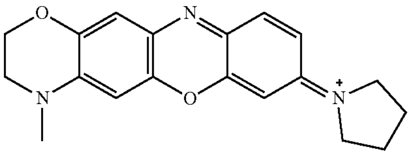

.

10. An imaging composition comprising an effective amount of a compound of claim 1 and a pharmaceutically or physiologically acceptable carrier.

11. A method of detecting nerves in a tissue or organ, the method comprising a) administering an effective amount of a composition comprising a compound of claim 1 to the tissue or organ to form a stained tissue or a stained organ; and b) imaging the stained tissue or stained organ, thereby detecting nerves intraoperatively in the stained tissue or stained organ.

* * * * *